United States Patent [19]

Fleer et al.

[11] Patent Number: 5,679,544
[45] Date of Patent: Oct. 21, 1997

[54] MODIFIED KLUYVEROMYCES YEASTS, THEIR PREPARATION AND USE

[75] Inventors: Reinhard Fleer, Bures sur Yvette; Alain Fournier, Chatenay Malabry; Patrice Yeh, Paris, all of France

[73] Assignee: Rhone-Poulenc Rorer S.A., Antony, France

[21] Appl. No.: 360,673

[22] PCT Filed: Jun. 23, 1993

[86] PCT No.: PCT/FR93/00623

§ 371 Date: Feb. 6, 1995

§ 102(e) Date: Feb. 6, 1995

[87] PCT Pub. No.: WO94/00579

PCT Pub. Date: Jan. 6, 1994

[30] Foreign Application Priority Data

Jun. 25, 1992 [FR] France .................................. 92 07785

[51] Int. Cl.[6] .......................... C12P 21/00; C12N 15/09; C12N 1/19; C12N 15/81
[52] U.S. Cl. .................. 435/69.1; 435/172.3; 435/254.2
[58] Field of Search ................................ 435/254.2, 69.1, 435/172.3

[56] References Cited

FOREIGN PATENT DOCUMENTS 0301670   1/1989   European Pat. Off. .
92/17595  10/1992  WIPO .

OTHER PUBLICATIONS

Fleer et al., "Stable multicopy vectors for high level secretion of recombinant human serum albumin by Kluyveromyces yeasts", Bio/Technology 9:968–975 Oct. 1991.

Sturley et al., "Secretion and lipid association of human apolipoprotein E in *Saccharomyces cerevisiae* requires a host mutation in sterol esterification uptake", J. Biol. Chem. 266:16273–16276 Sep. 1991.

Chem. Abstracts Abstract 120893j 99(15):520, 1983, Grieve Kitchen Dulley Bartley, Partial Characterization of Cheese–Ripening Proteinases Produced by the Yeast *Kluyveromyces lactis*.

FEBS Letters 234(2):464–70, 1988, Tanguy–Rougeau Wesolowski–Lou Fukuhara, The *Kluyveromyces lactis* KEX1 Gene Encodes a Subtilisin–Type Serine Proteinase.

Cell 48:887–97, 1987, Valls Hunter Rothman Stevens, Protein Sorting in Yeast: The Localization Determinant of Yeast Vacuolar Carboxypeptidase Y Resides in.

Molec. Cell Biol. 7(12):4390–99, 1987 Moehle Tizard Lemmon Smart Jones, Protease B of the Lysosomelike Vacuole of the Yeast *Saccharomyces cerevisiae* Is Homologous to the Subtilisin.

Nucleic Acids Res. 17(4): 1779, 1989, Lott Page Boiron Benson Reiss, Nucleotide Sequence of the *Candida albicans* Aspartyl Proteinase Gene.

EP 336056, filing date Jan. 24, 1989, Publ Date Oct. 11, 1989, Yamamoto, Protease.

Primary Examiner—Jasemine C. Chambers
Assistant Examiner—Scott D. Priebe

[57] ABSTRACT

The present invention concerns yeasts of the genus Kluyveromyces having one or more genetic modifications of at least one gene coding for a protease, said gene reducing or modifying the proteolytic actively of said yeasts, as well as their use as a cellular host for the secretion of recombinant proteins.

13 Claims, 12 Drawing Sheets

FIG. 5

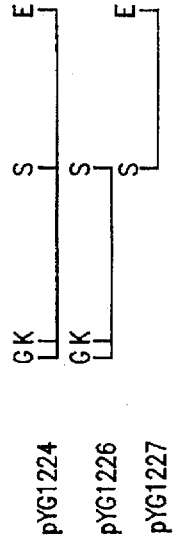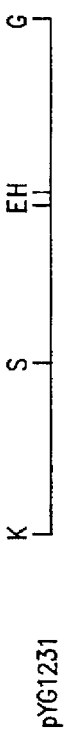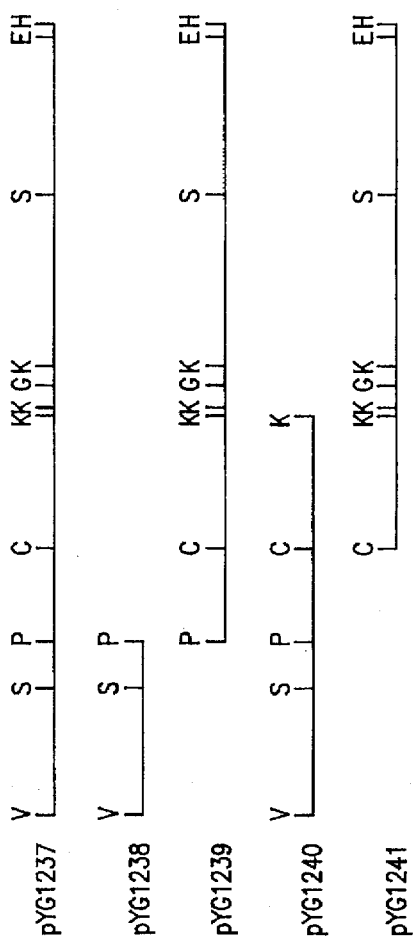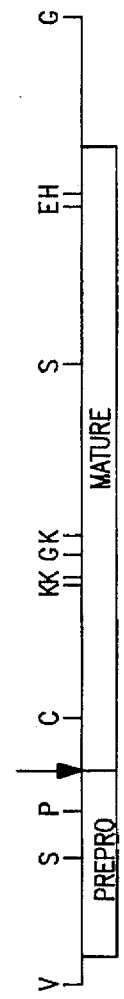
FIG. 6A
FIG. 6B
FIG. 6C
FIG. 6D

MODIFIED KLUYVEROMYCES YEASTS, THEIR PREPARATION AND USE

The present invention relates to new genetically modified yeasts belonging to the genus Kluyveromyces and to their use to produce advantageously recombinant proteins.

The advances accomplished in the field of molecular biology have made it possible to modify microorganisms in order to make them produce proteins of interest and for example heterologous proteins (mammalian proteins, artificial proteins, chimetic proteins, and the like). In particular, numerous genetic studies have been performed on the bacterium *Escherichia coli* and the yeast *Saccharomyces cerevisiae*. More recently, genetic tools have been developed so as to use the yeast Kluyveromyces as host cell for the production of recombinant proteins. The discovery of the plasmid pKD1, derived from *K.drosophilarum* (EP 241 435), has made it possible to develop a particularly advantageous host vector system for the secretion of recombinant proteins (EP 361 991, EP 413 622).

However, the application of this system of production is still limited, in particular by the problems.of the efficacy of gene expression in these recombinant microorganisms, by the problems of stability of the plasmids and also by the problems of degradation of the recombinant products by the cells in which they are synthesized. A proteolysis phenomenon can indeed manifest itself during transit of the protein of interest in the secretory pathway of the recombinant yeast, or by the existence of secreted proteases or proteases present in the culture medium following an undesirable cell lysis which occurs during fermentation.

The applicant has now shown that it is possible to improve the levels of production of the said recombinant proteins, that is to say in their integral form, in Kluyveromyces yeasts, by modifying at least one gene encoding a cellular protease, and especially a protease transiting through the secretory pathway. Surprisingly, the applicant has furthermore shown that such modifications are particularly advantageous since they make it possible to increase the levels of production of recombinant proteins, and this is all the more advantageous since the said modification is without apparent effect on the growth rate and the viability of the modified cells under industrial fermentation conditions. Still surprisingly, the applicant has also shown that the said modifications do not affect the stability of the transformant yeasts, which makes it possible to use the said yeasts in a particularly advantageous manner to produce recombinant proteins.

The subject of the present invention is therefore yeasts of the genus Kluyveromyces having one or more genetic modifications of at least one gene encoding a protease, modifying the proteolytic activity of the said yeasts. Preferably, the genetic modification(s) render the said gene partially or totally incapable of encoding the natural protease. In another preferred embodiment of the invention, the gene(s) thus genetically modified encode a non-functional protease, or a mutant having a modified proteolytic activity spectrum. In another preferred embodiment of the invention, the gene(s) encoding the said proteases are placed under the control of a regulated promoter.

The yeasts of the genus Kluyveromyces according to the invention comprise the yeasts as defined by van der Walt [in: The Yeasts (1987) N. J. W. Kregervan Rij (ed): Elsevier: p.224], and preferably the yeasts *K.marxianus* var.*lactis* (*K.lactis*), *K.marxianus* var. *marxianus* (*K.fragilis*), *K.marxianus* var. *drosophilarum* (*K.drosophilarum*), *K.waltii*, and the like.

Genetic modification should be understood to mean more particularly any suppression, substitution, deletion or addition of one or more bases in the gene(s) considered. Such modifications can be obtained in vitro (on isolated DNA) or in situ, for example, by means of genetic engineering techniques, or alternatively by exposing the said yeasts to a treatment by means of mutagenic agents. As mutagenic agents, there my be mentioned for example physical agents such as energetic radiation (X, g, ultra violet rays and the like), or chemical agents capable of reacting with various functional groups of the bases of DNA, and for example alkylating agents [ethyl methanesulphonate(EMS), N-methyl-N'-nitro-N-nitrosoguanidine, N-nitroquinoline 1-oxide (NQO)], bialkylating agents, intercalating agents and the like. Deletion is understood to mean any suppression of the gene considered. It may relate in particular to a part of the region encoding the said proteases and/or of all or part of the transcriptional promoter region.

The genetic modifications can also be obtained by gens disruption, for example according to the procedure initially described by Rothstein [Meth. Enzymol. 101 (1983) 202]. In this case, the entire coding sequence will be preferably disrupted so as to allow the replacement, by homologous recombination, of the wild-type genomic sequence by a non-functional or mutant sequence.

The said genetic modification(s) may be located in the gene encoding the said proteases, or outside the region encoding the said proteases, for example in the regions responsible for the transcriptional expression and/or regulation of the said genes. The inability of the said genes to encode the natural proteases can manifest itself either by the production of a protein which is inactive because of structural or conformational modifications, or by the absence of production, or by the production of a protease having a modified enzymatic activity, or alternatively by the production of the natural protease at an attenuated level or according to a desired mode of regulation.

Moreover, certain modifications such as point mutations are by nature capable of being corrected or attenuated by cellular mechanisms, for example during the replication of DNA preceding cell division. Such genetic modifications are thereby of limited interest at the industrial level since the phenotypic properties resulting therefrom are not perfectly stable. The applicant has now developed a process which makes it possible to prepare Kluyveromyces yeasts having one or more genetic modifications of at least one gene encoding a protease, the said modification(s) being segregationally stable and/or non-reversible. The yeasts having such modifications are particularly advantageous as cellular host for the production of recombinant proteins. The invention also makes it possible to produce yeasts in which the modification(s) made render the gene(s) considered totally or only partially incapable of producing a functional protease.

Preferably the yeasts according to the invention have one or more segregationally stable genetic modifications. Still according to a preferred embodiment, the genetic modification(s) its non-reversible. Still according to a preferred embodiment of the invention, the genetic modification(s) leave(s) no residual activity for the gens considered.

Preferably, the gene(s) encoding one or more proteases are chosen from the genes encoding proteases transiting through the secretorypathway of Kluyveromyces. Such proteases may be located in the endoplasmic reticulum, the compartment of the Golgi apparatus, the post-Golgi compartment, and for example the cellular vacuoles, the vesicles of the endosome, the secretion vesicles, or the extracellular medium.

As example of such genes, there may be mentioned the Kluyveromyces genes encoding a protease chosen from the families comprising protease A, protease B, or a carboxypeptidase (and for example carboxypeptidase Y or carboxypeptidase S), or alternatively endopeptidase KEX1 of *K. lactis* or a protease with similar activity, and for example protease YAP3 [Egel-Mitani et al., Yeast 6 (1990) 127], or more generally any other protease involved in the maturation of certain secreted proteins.

In a preferred embodiment of the invention, the considered gene(s) encode proteases which are not involved in the cleavage of the signal peptide of the recombinant proteins expressed in the form of preproteins. There may be mentioned by way of examples of particularly useful genes the genes for protease A, for protease B, and for carboxypeptidase Y of Kluyveromyces, whose cloning is described in the examples.

In another embodiment of the invention, the said protease(s) possess(es) a signal peptidase activity and the said genetic modification(s) allow their overexpression, which is particularly advantageous in the case or this step is a limiting step of the secretorypathway.

The subject of the invention is also any Kluyveromyces yeast as defined above into which an exogenous DNA sequence comprising one or more genes encoding a protein of interest which it is desired to express and/or secrete in the said yeast, has been introduced.

For the purposes of the present invention exogenous DNA sequence is understood to mean any DNA sequence introduced artificially into the yeast and encoding one or more proteins of interest. In particular, this may be complementary DNA (cDNA) sequences, artificial or hybrid sequences, or alternatively synthetic or semi-synthetic sequences, which are included in an expression cassette permitting synthesis in the said yeasts of the said protein(s) of interest. For example, this exogenous DNA sequence may include a region for initiation of transcription, regulated or otherwise in Kluyveromyces, so as to direct, when desirable, the expression of the said proteins of interest.

Preferably, the exogenous DNA sequence is included in a vector, which may be capable of autonomous replication in the yeast considered, or of the integrative type. More particularly, autonomously replicating vectors can be prepared from autonomously replicating sequences in Kluyveromyces, and for example this may be the plasmid pKD1 [Falcone et al., Plasmids 15 (1986) 248; Chen et al., Nucl. Acids Res. 14 (1986) 4471] characterized by a high segregational stability and especially in the various varieties of *K. marxianus*, or the plasmid pEW1 isolated in *K. waltii* [Chen et al., J. General Microbiol. 138 (1992) 337]. Autonomously replicating vectors can also be prepared from chromosomal sequences (ARS). As regards the integrarive-type vectors, these can be prepared from chromosomal sequences homologous to the said host yeast, so as to flank the genetic sequence encoding the said proteins of interest, and a genetic selectable marker, so as to orient the integration of the whole by homologous recombination. In a specific embodiment, the said homologous sequences correspond to genetic sequences derived from the coding region of the said protease, which makes it possible to replace by homologous recombination the original sequence of the said protease by the selectable marker and the exogenous DNA sequence, while permitting gene disruption of the said protease. In another embodiment, the expression cassette is integrated at the locus encoding the ribosomal RNAs (rDNA) permitting gens amplification of the said expression cassette [Bergkamp et al., Curr. Genet. 21 (1992) 365]. Still in another embodiment, the exogenous DNA sequence is integrated into the chromosome of the said host yeasts by non-homologous recombination.

The exogenous DNA sequence can be introduced into the yeast by the techniques practised by persons skilled in the art, and for example recombinant DNA techniques, genetic crossings, protoplast fusion, and the like. in a specific embodiment, the exogenous DNA sequence is introduced into Kluyveromyces yeasts by transformation, electroporation, conjugation, or any other technique described in the literature. As regards transformation of the Kluyveromyces yeasts, the technique described by Ito et al. [J. Bacteriol. 153 (1983) 163] can be used. The transformation technique described by Durrens et al. [Curr. Genet. 18 (1990) 7] using ethylene glycol and dimethyl sulphoxide is also effective. It is also possible to transform the yeasts by electroporation, according to the method described by Karube et al. [FEBS Letters 182 (1985) 90]. An alternative procedure is also described in Patent Application EP 361 991.

The said Kluyveromyces yeasts modified for their protease content by the techniques described above are advantageously used as host cells to produce recombinant proteins, and for example heterologous proteins of pharmaceutical or dietary interest. The said host yeasts are particularly advantageous since they make it possible to increase the quality and quantity of recombinant proteins which it is desired to produce and/or secrete, and since the said genetic modifications of the said cells do not affect the genetic and mitotic stability of the vectors for expression of the said recombinant proteins. Another subject of the invention therefore lies in a process for producing recombinant proteins according to which a yeast as defined above is cultured under conditions for expressing the protein(s) encoded by the exogenous DNA sequence, and the protein(s) of interest is (are) recovered. In a preferred embodiment, the said proteins of interest are secreted into the culture medium. As example, there may be mentioned naturally occurring proteins, or artificial proteins, and for example hybrid proteins. In this case, the use of yeast cells having a modified protease content is particularly advantageous because of the exposure of the hinge region between the various protein domains of the chimera. In a specific embodiment, the said artificial protein contains a peptide fused to one of the ends of the chimera and is particularly sensitive, for example during transit in the secretory pathway, to a proteolytic degradation by an N- or C-terminal exoprotease, and for example a carboxypeptidase. It is understood that the proteolytic degradation of the protein of interest can also result from any cellular protease, and for example cytoplasmic protease, released into the external medium because of an undesirable cell lysis during the fermentation process of the said recombinant yeasts. Genetic modification of the nucleotide sequence encoding such proteases can therefore also result in a particularly advantageous process for producing the said proteins of interest and is also claimed.

Preferably, the process according to the invention allows the production of proteins of pharmaceutical or dietary interest. As example, there may be mentioned enzymes (such as in particular superoxide dismutase, catalase, amylases, lipases, amidases, chymosin and the like, or any fragment or derivative thereof), blood derivatives (such as serum albumin, alpha- or beta-globin, coagulation factors, and for example factor VIII, factor IX, von Willebrand's factor, fibronectin, alpha-1 antitrypsin, and the like, or any fragment or derivative thereof), insulin and its variants, lymphokines [such as interleukins, interferons, colony-stimulating factors (G-CSF, GM-CSF, M-CSF and the like), TNF and the like, or any fragment or derivative thereof], growth factors (such as growth hormone, erythropoietin, FGF, EGF, PDGF, TGF, and the like, or any fragment or derivative thereof), apolipoproteins and their molecular variants, antigenic polypeptides for the production of vaccines (hepatitis, cytomegalovirus, Epstein-Barr virus, herpes virus and the like), or alternatively polypeptide fusions such as especially fusions containing a biologically active part fused to a stabilizing part. The proteins may comprise an exporting sequence for secretion.

Another subject of the present invention lies in a Kluyveromyces DNA fragment encoding a protease. The Applicant has indeed detected, isolated and characterized certain Kluyveromyces proteases and especially proteases transiting through the secretcry pathway. More preferably, one of the subjects of the invention relates to a Kluyveromyces protease chosen especially from proteases A, B, carboxypeptidase Y, as well as the family of serine proteases of the subtilisin type and of which one representative is the K. lactis KEX1 protease [Wésolowski-Louvel et al., Yeast A (1988) 71]. By way of example, the nucleotide sequences of the K. lactis genes encoding proteases A, B and carboxypeptidase Y were determined by the Applicant and are presented SEQ ID No. 5, 1 and 2 respectively. A restriction map of a chromosomal fragment encoding K. lactis protease A is also presented in FIG. 10. It is understood that any genetic variant of these protease genes, and their advantageous use for producing proteins of interest, also form part of the invention. The said variations may be of natural origin, but may also be obtained in situ or in vitro by genetic engineering techniques, or after treating the cells with a mutagenic agent, and include in particular point or multiple mutations, deletions, additions, insertions, hybrid proteases and the like. In a still more specific embodiment, the genetic variations may also relate to the regions for controlling the expression of the said proteases, for example so as to modify their levels of expression or their mode of regulation.

The subject of the invention is also any protein resulting from the expression of an exogenous DNA fragment as defined above.

The subject of the invention is also a process for preparing a genetically modified Kluyveromyces yeast and its advantageous use for producing proteins of interest. Preferably, the process of the invention consists in replacing the chromosomal gene(s) considered by a version modified in vitro.

The present invention will be more fully described with the aid of the following examples which should be considered as illustrative and non-limitative.

BRIEF DESCRIPTION OF THE DRAWING

The representations of the plasmids indicated in the following figures are drawn to a rough scale and only the restriction sites which are important for understanding the clonings carried out are indicated.

FIG. 5: Comparison of the protein sequence of the BglII-EcoRI fragment of K. lactis genomic DNA (residues $Arg^{308}$ to $Phe^{531}$ of the peptide sequence SEQ ID No. 1) with the corresponding part of the S. cerevisiae PRB1 gene (SEQ ID NO. 8) (residues $Arg^{105}$ to Leu328). The asterisks indicate the amino acids conserved between the two sequences.

FIGS. 6A-D: Restriction maps of the genomic inserts of plasmids pYG1224, pYG1226 and pYG1227 (panel A); pYG1231 (panel B); pYG1237, pYG1238, pYG1239, pYG1240, pYG1241 and pYG1242 (panel C). The position of the cleavage sites of the following endonucleases is indicated: G=BglII; C=ClaI; S=SalI; E=EcoRI; H=HindIII; K=KpnI; P=PstI; V=EcoRV. Panel D: location of the coding phase of the K. lactis PRB1 gene; the vertical arrow indicates the rough position of the N-terminal end of the mature protein. The position of the codon presumed to be for initiation of translation and the position of the translational stop codon are indicated by an asterisk.

K=KpnI; X=XhoI; the HindIII cloning site is derived from the vector and is underlined. Panel B: Disruption of the *K. lactis* PRB1 gene by the selectable marker URA3 from *S. cerevisiae*. This Southern blot corresponds to the genomic DNA of *K. lactis* CBS 294.91 (uraA) after transformation by the BglII-EcoRI fragment of panel A and selection in the absence of uracil. Wells 1 to 3: genomic DNA of three transformants after BglII+EcoRI double restriction; the strain of well 3 is *K. lactis* Y750; well 4: genomic DNA of the strain CBS 294.91 after BglII+EcoRI double restriction. The radioactive probe used corresponds to the BglII-EcoRI fragment of the plasmid pYG1224 (FIG. 6A).

FIGS. 10A–D: Restriction map of the inserts of the plasmids pC34 [vector KEp6; panel a)], pYG154 [vector pIC-20R; panel b)] and pYG155 [vector pIC-20R; panel c)]. Panel d): fragment used for the disruption. The restriction sites in brackets were destroyed with the Klenow enzyme or with T4 DNA polymerase as indicated in the text. The box corresponds to the *K. lactis* genomic insert and the line corresponds to the sequences of the vectors. List of abbreviations: C=ClaI; H=HindIII; B=BamHI; E=EcoRI; P=PstI; S=SalI, Sp=SphI; Sau=Sau3A; Sm=SmaI; N=NcoI.

Figure 11:
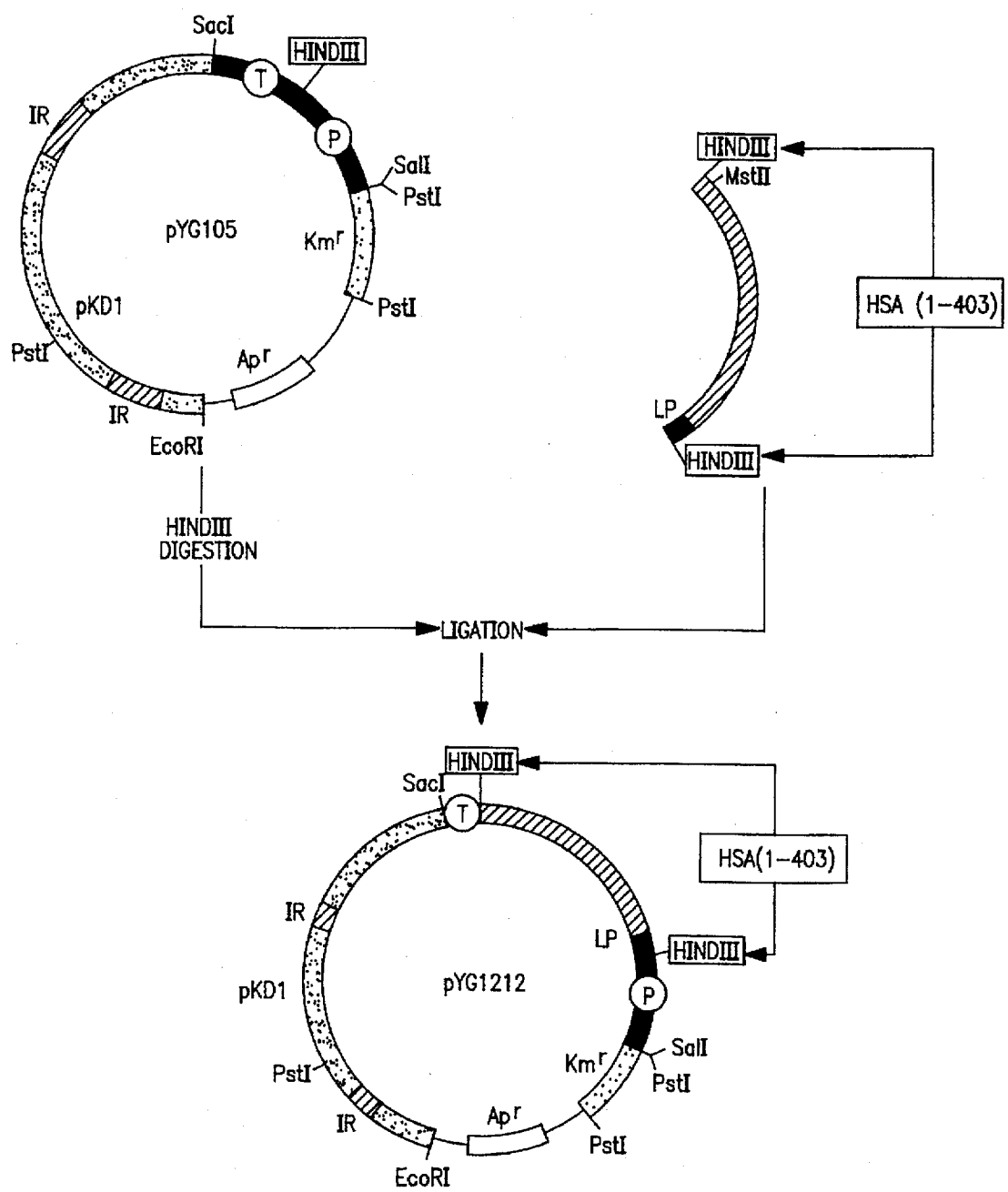

FIG. 11: Restriction map of the plasmid pYG105 and strategy for constructing the plasmid pYG1212. Abbreviations used: P, *K. lactis* LAC4 promoter T, transcriptional terminator; IR, inverted repeat sequences of the plasmid pKD1; LP, prepro region of HSA; Ap$^r$ and Km$^r$ designate respectively the genes for resistance to ampicillin (*E. coli*) and to G418 (Kluyveromyces).

Figure 12:
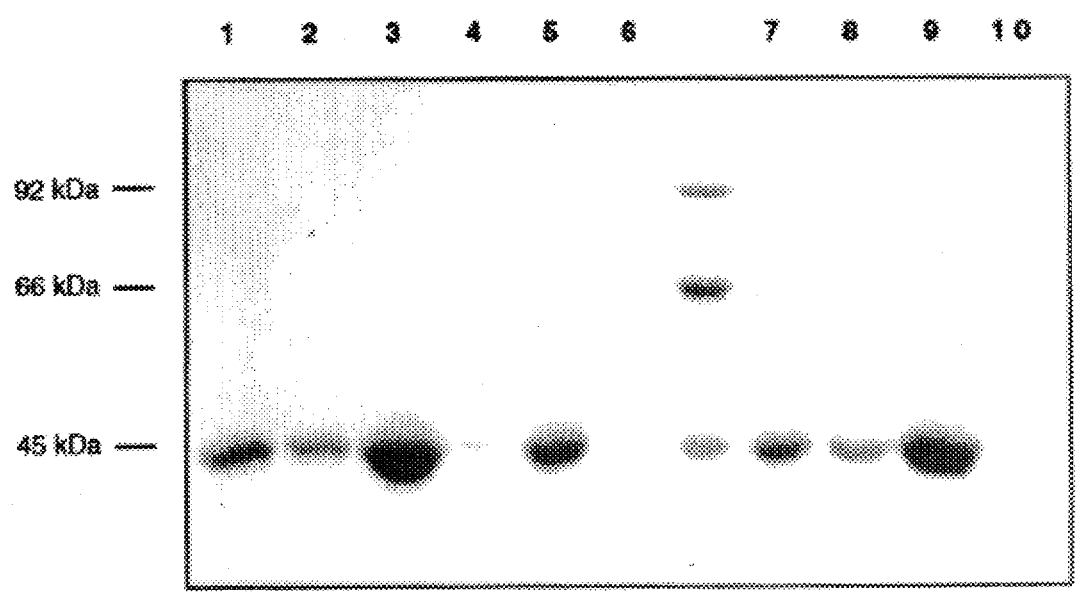

FIG. 12: Comparison of the capacities of secretion of a truncated variant of human albumin in the *K. lactis* CBS 293.91 strains (wells 2, 4, 6, 8 and 10) or its disrupted mutant for the gene for protease B (strain Y750; wells 1, 3, 5, 7 and 9), after transformation with the plasmid pYG1212. The transformant cells are cultured in Erlenmeyer flasks in the presence of G418 (200 mg/l) for 2 days (wells 1, 2, 7 and 8), 4 days (wells 3, 4, 9 and 10), or 7 days (wells 5 and 6); wells 1 to 6 correspond to growth in YPD medium, and wells 7 to 10 correspond to growth in YPL medium. The spots are equivalent to 50 ml of culture supernatents.

GENERAL CLONING TECHNIQUES

The methods conventionally used in molecular biology, such as the preparative extractions of plasmid DNA, the centrifugation of plasmid DNA in caesium chloride gradient, electrophoresis on agarose or acrylamide gels, purification of DNA fragments by electroelution, extractions of proteins with phenol or phenol-chloroform, DNA precipitation in saline medium with ethanol or isopropanol, transformation in *Escherichia coli*, and the like are well known to persons skilled in the art and are widely described in the literature [Maniatis T. et al., "Molecular Cloning, a Laboratory Manual", Cold Spring Harbor Laboratory, Cold Spring Harbor, N.Y., 1982; Ausubel F. M. et al., (eds), "Current Protocols in Molecular Biology", John Wiley & Sons, New York, 1987].

The restriction enzymes were provided by New England Biolabs (Biolabs), Bethesda Research Laboratories (BRL) or Amersham and are used according to the recommendations of the suppliers.

The pBR322 and pUC type plasmids and the phages of the M13 series are of commercial origin (Bethesda Research Laboratories). The pIC type plasmids have been described by Marsh et al. [Gene 32. (1984) 481].

For the ligations, the DNA fragments are separated according to their size by electrophoresis on agarose or acrylamide gels, extracted with phenol or with a phenol/chloroformmixture, precipitated with ethanol and then incubated in the presence of phage T4 DNA ligase (Biolabs) according to the recommendations of the supplier.

The filling of the protruding 5' ends is carried out by the Klenow fragment of DNA polymerase I of *E. coli* (Biolabs) according to the specifications of the supplier. The destruction of the protruding 3' ends is carried out in the presence of phage T4 DNA polymerase (Biolabs) used according to the recommendations of the manufacturer. The destruction of the protruding 5' ends is carried out by a controlled treatment with S1 nuclease. The exonuclease Ba131 is used according to the recommendations of the supplier (Biolabs).

The oligodeoxynucleotides are synthesized chemically according to the phosphoramidite method using β-cyanoethyl protective groups [Sinha et al., Nucleic Acids Res. 12 (1984) 4539]. After synthesis, the protective groups are removed by treatment with ammonium hydroxide and two precipitations with butanol make it possible to purify and concentrate the oligodeoxynucleotides [Sawadogo and Van Dyke, Nucleic Acids Res. 19 (1991) 674]. The DNA concentration is determined by measuring the optical density at 260 nm.

Site-directed mutagenesis in vitro with synthetic oligodeoxynucleotides is carried out according to the method developed by Taylor et al. [Nucleic Acids Res. 13 (1985) 8749] using the kit distributed by Amersham.

The DNA fragment used to serve as molecular probe on the *K. lactis* genomic DNA is amplified in vitro by the PCR technique [Polymerase-catalysed Chain Reaction, Saiki R. K. et al., Science 230 (1985) 1350; Mullis K. B. and Faloona F. A., Meth. Enzym. 155 (1987) 335] on the *S. cerevisiae* DNA. The amplification is automated (40 amplification cycles) and is carried out in a Perkin Elmer Cetus apparatus (DNA thermal cycler) using the Taq polymerase (isolated from the archaebacterium *Thermophilus aquaticus*) provided by the company Perkin Elmer. Each amplification cycle comprises three stages:

1) A stage for denaturation of DNA at 91° C.;

2) A stage for hybridization of oligodeoxynucleotide primers onto the template DNA. The hybridization temperature is chosen five to ten degrees below the melting temperature of the oligodeoxynucleotides ($T_{1/2}$). For oligodeoxynucleotides of about 20 mer in size, $T_{1/2}=2x(A+T)+4x(C+G)$ [Itakura et al., Ann. Rev. Blochem. 53 (1984) 323].

3) A stage for synthesis of complementary DNA by Taq polymerase at 72° C.

The preparation of the radioactive nucleotide probes is carried out by incorporation of radioactive adCTP (phosphorus 32) along the length of the molecule neosynthesized from 20 ng of DNA using the "Random Primed DNA Labeling" kit marketed by the firm Boehringer.

The transfers of DNA onto nylon membrane (Biodyne, Pall, St Germain en Laye) or nitrocellulose (Schleicher & Schuell, Dassel) are carried out according to the method initially developed by Southern [J. Mol. Biol. 98 (1979) 503]. The hybridization and washing conditions used depend on the nature of the probe used: under heterologous conditions (*K. lactis* genomic DNA hybridized with a probe from *S. cerevisiae* for example), the hybridization and the washes are carried out under conditions which are not very stringent (hybridization for 15 hours at 40° C. without formamide in 5X SSC/5X Denhart, the filter is then washed 3 times in 5X SSC/1% SDS at 40° C. for 15 minutes, then once in 0.25X SSC/1% SDS for 10 minutes); under homologous conditions (*K. lactis* genomic DNA hybridized with a probe from *K. lactis* for example), the hybridization and the washes are carried out under more stringent conditions (hybridization for 15 hours at 40° C. in 5X SSC/SX Denhart/ 50% formamide, the filter is then washed 3 times in 5X SSC/1% SDS at 40° C. for 15 minutes, then once in 0.2X SSC/1% SDS for 10 minutes).

The verification of the nucleotide sequences is carried out on plasmid DNA with the "Sequenase version 2.0" kit from the Company United States Biochemical Corporation, according to the method by Tabor and Richardson [Proc. Natl. Acad. Sci. USA 84 (1987) 4767]. This technique is a modification of the method initially described by Sanger et al. [Proc. Natl. Acad. Sci. USA 74 (1977) 5463].

The transformations of *K. lactis* with DNA from the plasmids for expression of the proteins of the present invention are carried out by any technique known to persons skilled in the art, and of which an example is given in the text.

Unless otherwise stated, the bacteria strains used are *E. coli* MC1060 (lacIPOZYA, X74, galU, galK, strA$^r$), *E. coli* TG1 (lac, proA, B, supE, thi,hsdDS/FtraD36, proA$^+$B$^+$, lacI$^q$,lacZ, M15), or *E. coli* JM101 [Messing et al., Nucl. Acids Res. 9 (1981) 309].

The yeast strains used belong to the budding yeasts and more particularly to yeasts of the genus Kluyveromyces. The *K. lactis* MW98-8C (a, uraA, arq, lys, K$^+$, pKD1°), *K. lactis* CBS 293.91, *K. lactis* CBS 294.91 (uraA), and *K. lactis* CBS 2359/152 [a, metA, (k1, k2); Wésolowski et al., Yeast 4 (1988) 71] strains were particularly used; a sample of the MW98-8C strain was deposited on 16 Sep. 1988 at Centraalbureau voor Schimmelkulturen (CBS) at Baarn (The Netherlands) where it was registered under the number CBS579.88.

The preparation of yeast genomic DNA is essentially derived from the technique by Hoffman and Winston [Gene 57 (1987) 267] and is described in detail in the text.

The yeast strains transformed with the expression plasmids encoding the proteins of the present invention are cultured in Erlenmeyer flasks or in 2 l pilot fermenters (SETRIC, France) at 28° C. in rich medium (YPD: 1% yeast extract, 2% Bactopeptone, 2% glucose; or YPL: 1% yeast extract, 2% Bactopeptone, 2% lactose) with constant stirring.

EXAMPLES

Example 1

CLONING OF THE *K. LACTIS* PROTEASE B GENE

E.1.1. Production of a probe by enzymatic amplification in vitro of a DNA sequence.

Figure 1:
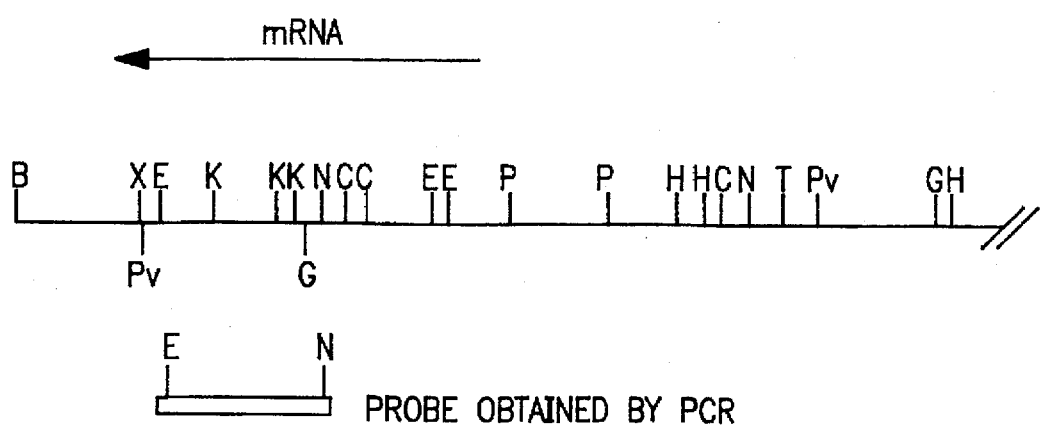
FIG. 1: Restriction map of the genomic insert of the plasmid pFP8. The position of the cleavage sites of the following endonucleases is indicated: B=BamHI; G=BglIII; C=ClaI; E=EcoRI; H=HindIII; K=KpnI; N=NcoI; P=PstI; Pv=PvuII; T=SstI; X=XhoI. The fragment obtained after PCR amplification is represented as well as the mRNA of the S. cerevisiae PRB1 gene.

An enzymatic amplification by PCR is carried out starting with the plasmid pFP8 [Moehle etal., Genetics 115 (1987) 255; FIG. 1], *E. coli/S. cerevisiae* shuttle vector derived from YEp13 and carrying the *S. cerevisiae* PRB1 gens and the oligodeoxynucleotides 5'-TGACACTCAAAATAGCG-3' (SEQ ID NO. 9) the codon corresponding to the Asp$^3$ residue is underlined) and 5'-AATATCTCTCACTTGAT-3' (SEQ ID NO. 10) (the codon of the complementary strand corresponding to the residue Ile$^{348}$ is underlined). The temperature for hybridization of the oligodeoxynucleotides is 45° C. and the reaction volume of 100 ml comprises: 10 ng of plasmid pFP8, the oligodeoxynucleotide primers, 10 ml of 10X PCR buffer [Tris-HCl pH=8.5 (100 mM); MgC12 (20 mM); KCl (100 EM); gelatin (0.01%)], 10 ml dNTP (dATP+dCTP+dGTP+dTTP, each at a concentration of 10 mM)], and 2.5 units of Taq polymerase. The addition of a drop of paraffin oil makes it possible to avoid evaporation during elevations of temperature during the amplification cycles. A DNA fragment of 1,039 base pairs is obtained, whose identity is verified by analysis of the positions of certain restriction sites and corresponding to virtually the entire amino acid sequence of the mature form of protease B (Asp$^3$ to Ile$^{348}$). This fragment is then purified by electroelution after migration on a 0.8% agarose gel and is used to prepare the radioactive probe according to the "Random Priming" method.

E.1.2. Preparation of yeast genomic DNA.

The yeasts (strain *K. lactis* MW98-SC) in stationary growth phase are centrifuged. After washing the pellet in sterile water, the latter is taken up in a solution containing: 2% Triton X100 (v/v); 1% SDS (w/v); 100 mMNaCl; 10 mMTris-HCl (pH=8); 1 mM EDTA. The yeasts are then ground in the presence of phenolchloroform by the mechanical action of glass beads added to the mixture which is vortexed for 2 minutes. The aqueous phase is then recovered after centrifugation and precipitated by addition of 2.5 volumes of ethanol. The DNA is taken up in TE so as to be subjected to purification on a caesium gradient. Starting with 1 litre of culture, 1 mg of high molecular weight genomic DNA (>>20kb) is obtained.

E.1.3. Search for the gene byhybridizationunder low stringency conditions.

Figure 2A:
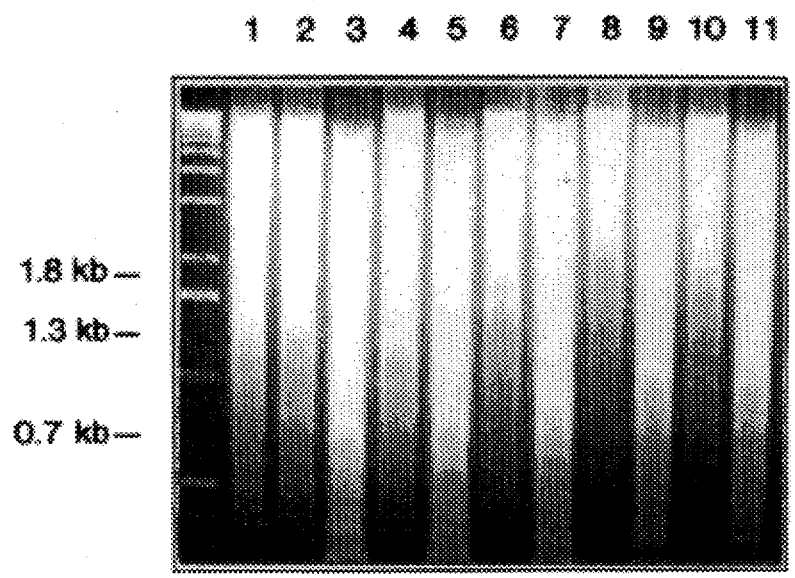
FIG. 2: Hybridization of the S. cerevisiae PRB1 probe with restriction fragments of the K. lactis genomic DNA. Top panel: photo of the agarose gel (1%) stained with ethidiumbromide and before transfer onto nylon filter; bottom panel: schematic representation of the signals obtained after hybridization of the filter with the radioactive probe. The numbering corresponds to the following digestions: 1=EcoRI; 2=BglII; 3=BglII+EcoRI; 4=HindIII; 5=HindIII+EcoRI; 6=PstI; 7=PstI+EcoRI; 8=SalI; 9=SalI+EcoRI; 10=BamHI; 11=BamHI+EcoRI.
Figure 2B:
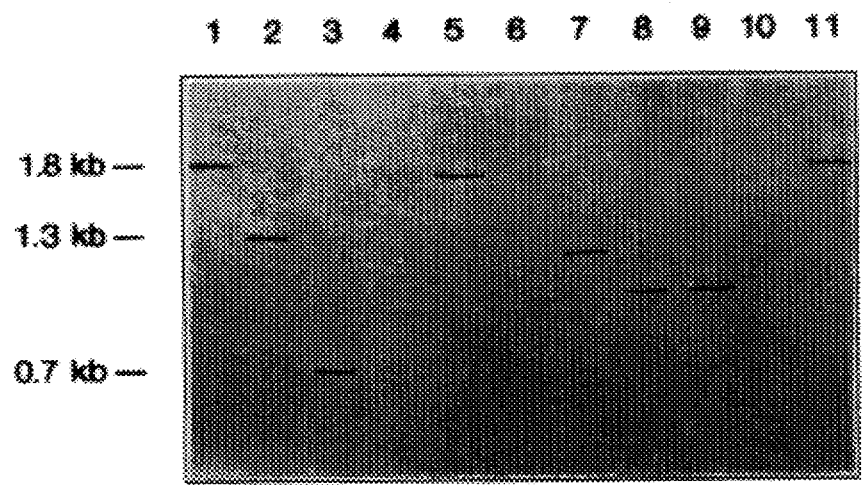

The genomic DNA preparation is subjected to total digestion with restriction enzymes whose sites are present in the multiple cloning site of the vector pIC-20H. A preliminary result shows that only conditions which are not very stringent (hybridization for 15 hours at 40° C. without formamide in 5X SSC/SX Denhart, then 3 washes in 5X SSC/1% SDS at 40° C. for 15 minutes, then 1 wash in 0.25X SSC/1% SDS for 10 minutes) make it possible to visualize an EcoRI fragment of 1.8 kb hybridizing with the *S. cerevisiae* PRB1 probe. A second Southern blotting is carried out in which each well contains 12 mg of genomic DNA cleaved for 15 hours with 20 units of EcoRI and 20 units of a second restriction enzyme (FIG. 2). Under the hybridization and washing conditions previously defined, a genomic fragment of about 700 bp and derived from the EcoRI+BglII double digestion hybridizes with the *S. cerevisiae* PRB1 probe (FIG. 2, well no. 3). Likewise, a BglII restriction fragment of greater size (about 1.3 kb) hybridizes with this probe (FIG. 2, well no. 2). The fragment of about 700 bp detected after digestion of the genomic DNA with EcoRI+BglII is therefore a BglII–EcoRI restriction fragment. The other restrictions appear to be less important since they generate either fragments which are smaller in size than that obtained by the EcoRI+BglII double digestion, or a fragment of identical size (1.8 kb) to that generated after digestion with EcoRI alone (FIG. 2, well no. 1).

Figure 3A:
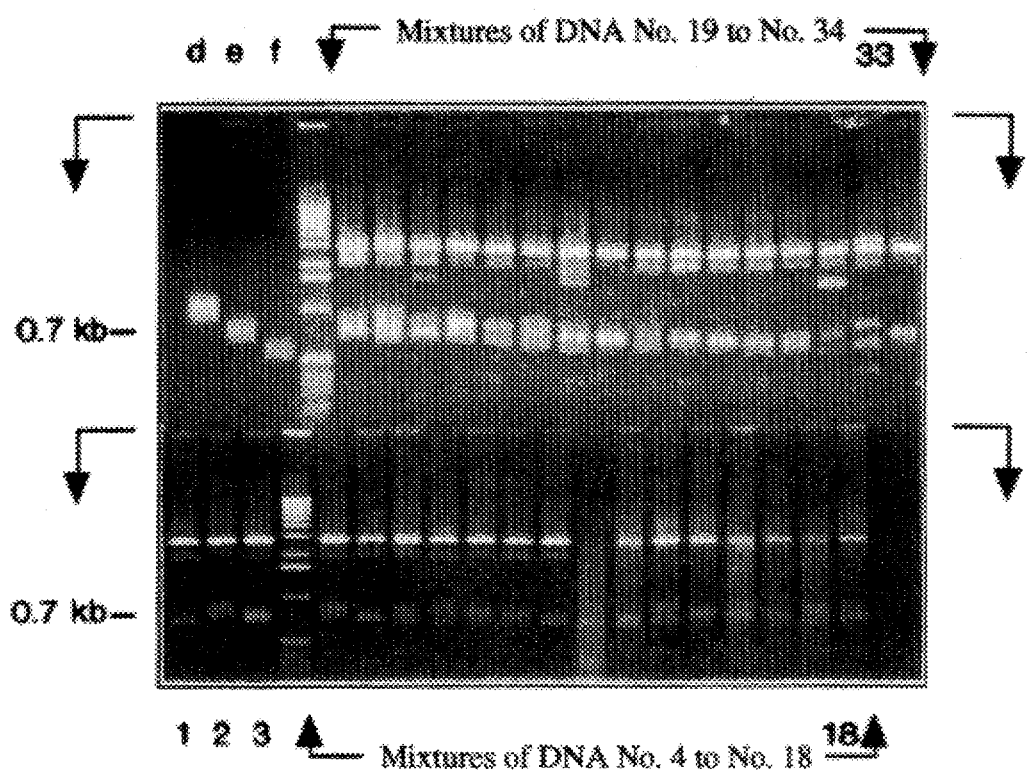
FIGS. 3A and B: Hybridization of the S. cerevisiae PRB1 probe with the 34 minipreparations of DNA (mixture of 10 clones each) after double restriction with the enzymes EcoRI and BglII. Panel A: photo of the agarose gel (1%) stained with ethidiumbromide and before transfer onto nylon filter; Panel B: autoradiography of the nylon filter after hybridization with the S. cerevisiae PRB1 probe; subfractions "d", "e" and "f" corresponding to an aliquot of the K. lactis genomic DNA fragments after total digestion with EcoRI+BglII and size fractionation by electroelution are indicated.
Figure 3B:
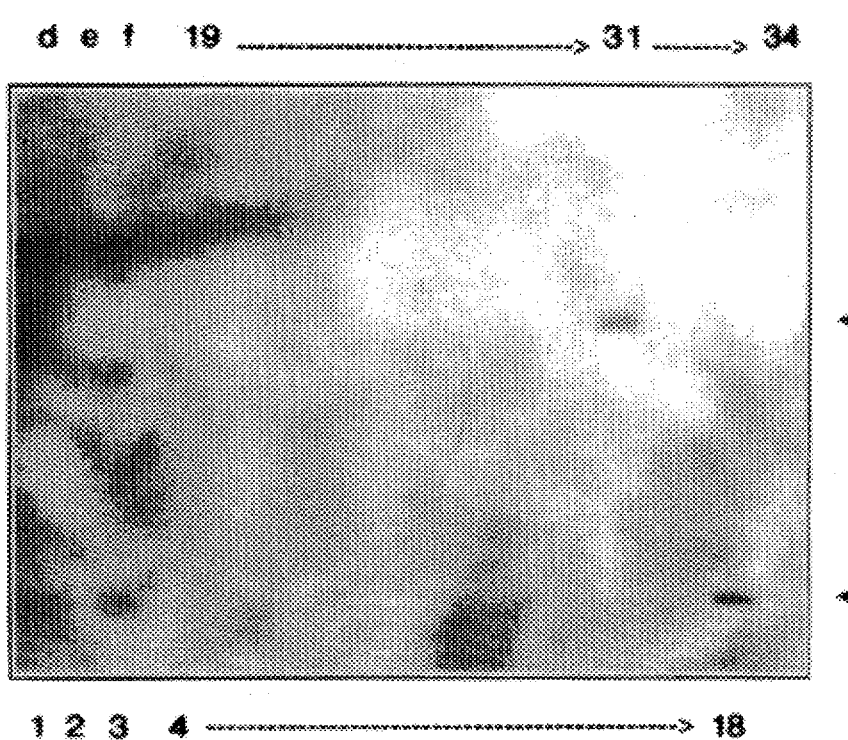

The cloning of this BglII–EcoRI asymmetric fragment of 700 bp makes it possible to obtain a fraction of the *K. lactis* PRB1 gene which can then serve as homologous probe for cloning the missing part(s) of the gene. To clone this fragment, 100 mg of genomic DNA are treated for 15 hours with 100 units of EcoRI and BglII endonucleases, then run on preparative agarose gel (1%). The fraction of the gel comprising the fragments whose size is between 500 and 1,000 bp is then cut into three subfractions (subfraction 500/700 bp; subfraction "e": 700/800 bp; subfraction "d": 800/1000 bp; FIG. 3). A Southern blotting carried out after running an aliquot of these subfractions and hybridization with the *S.*

Figures 4A, 4B:
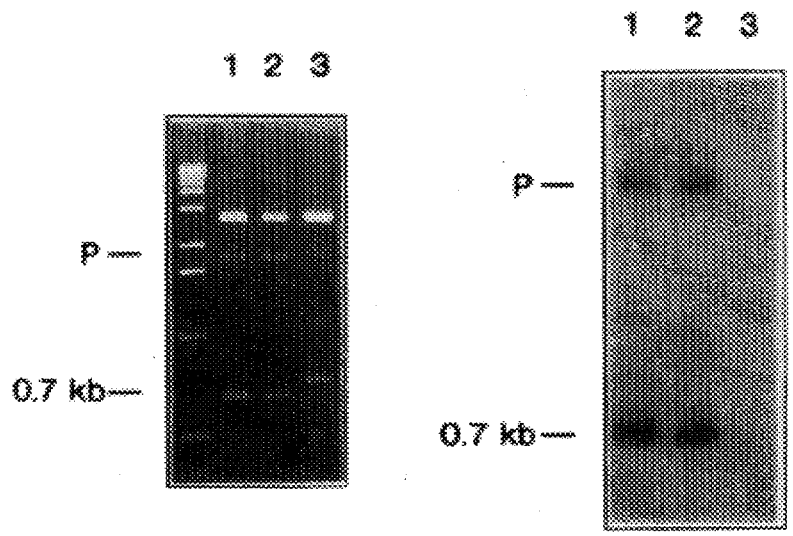
FIGS. 4A and B: Control hybridization of the positive clones 18-3 and 31-I. Panel A: photo after running on 1% agarose gel of EcoRI+BglII digests of the DNA of clones 31-I (well no. 1), 18-3 (well no. 2) and 31-K (negative control, well no. 3). Panel B: autoradiography of the nylon filter corresponding to the preceding gel after hybridization with the S. cerevisiae PRB1 probe. P corresponds to the location of the undigested plasmid (pYG1224); the position of the BglII-EcoRI restriction fragment of about 0.7 kb hybridizing with the radioactive probe is indicated.

*cerevisiae* PRB1 probe shows a hybridization signal of the expected size (700 bp) and particularly intense with the subfraction "e" (700/800 bp). A genomic library restricted to the BglII–EcoRI fragments of this subfraction (minigenomic library) is therefore constructed by cloning the BglII–EcoRI restriction fragments into the corresponding sites of the vector pIC-20H. The transformation of the ligation in *E. coli* gives 90% of white clones in LB dishes supplemented with ampicillin and X-gal. 340 clones (including about 30 blue clones) are then subcultured on the same medium so as to isolate them. The 340 clones of the restricted library are then divided into 34 mixtures each corresponding to 10 different clones and their DNA is digested with EcoRI+BglII, run on agarose gel, transferred onto membrane so as to then be hybridized with the *S. cerevisiae* PRB1 probe under hybridization and washing conditions which are not very stringent. FIG. 3 shows this Southern blot where two mixtures (no. 18 and no. 31) show a hybridization signal of the expected size (about 700 bp). The same operation is carried out in order to analyse separately the 10 clones of mixtures no. 18 and no. 31: clone no. 3 is the only clone of the mixture no. 18 to have a hybridization signal at the expected size (clone 18-3); in a similar manner, only clone I of the mixture 31 (clone 31-I) gives a hybridization signal at the expected size. A last Southern blotting is carried out starting with the DNA of clones 18-3 and 31-I (positive signal) and a negative clone (clone K of mixture no. 31). Under the hybridization and washing conditions previously defined, only clones 18-3 and 31-I confirm the presence of a positive signal after EcoRI+ BglII double digestion, whose size seems to be strictly equivalent (FIG. 4).

E.1.4. Identification of the gene.

The nucleotide sequence of the BglII–EcoRI fragment of clone 18-3 is produced in order to demonstrate that this fragment indeed corresponds to a fraction of the *K. lactis* PRB1 gene.

Figure 5:
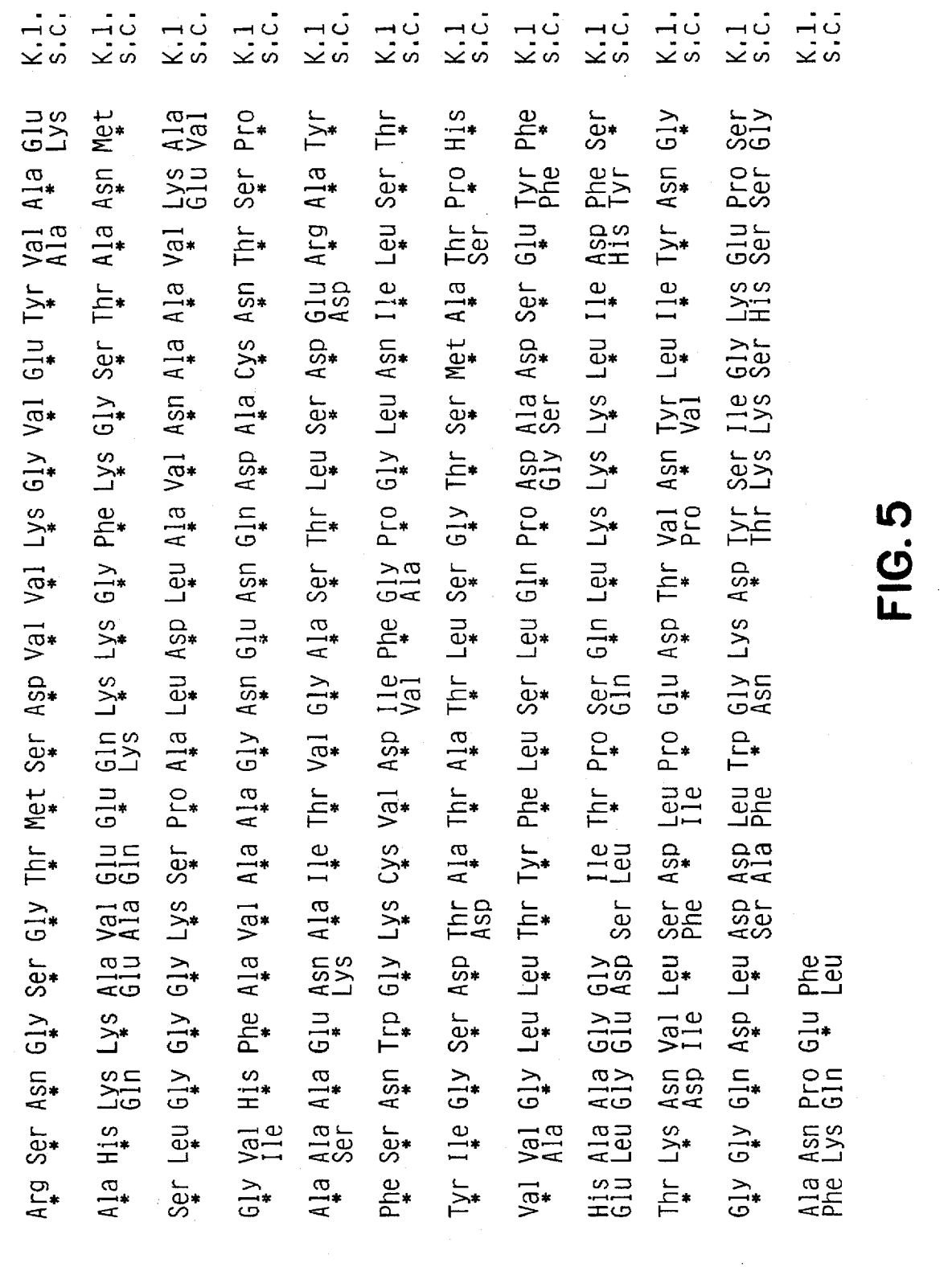

A rough restriction map of the plasmid pYG1224 from clone 18-3 is first produced and reveals the presence of an apparently unique SalI site at the centre of the BglII–EcoRI fragment. The BglII–SalI (about 350 bp) and SalI–EcoRI (about 300 bp) fragments of the plasmid pYG1224 are then cloned into the vector pUC19, which generates the plasmids pYG1226 and pYG1227 respectively (FIG. 6, panel A). The inserts of these plasmids are then sequenced in full using "universal primers". As indicated in FIG. 5, the BglII–EcoRI fragment of the plasmid pYG1224 contains an open reading frame (225 residues) which exhibits sequence homologies with a fragment of the *S. cerevisiae* PRB1 gene (Arg$^{105}$ to Leu$^{328}$). The presence of such a homology, as well as the strict conservation of the amino acids invariably found in the serine proteases of the subtilisin family demonstrate that the genomic DNA fragment carried by the plasmid pYG1224 indeed corresponds to a fragment of the *K. lactis* PRB1 gene.

E.1.5. Cloning of the 3' part of the gene.

The BglII–EcoRI fragment of the plasmid pYG1224 contains a unique KpnI restriction site located downstream of the BglII site (FIG. 6, panel A). The KpnI–EcoRI restriction subfragment of about 665 nucleotides is therefore generated from this fragment, isolated by electroelution after running on a 1% agarose gel and radioactively labelled by the "random priming" method. This radioactive probe is then used to determine the size of the restriction fragments of the *K. lactis* genomic DNA which include it. A KpnI–BglII fragment of about 1.2 kb is thus detected after hybridization and washing under stringent conditions (hybridization for 15 hours at 40° C. in 5X SSC/5X Denhart/ 50% formamide, then 3 washes in 5X SSC/1% SDS at 40° C. for 15 minutes, then 1 wash in 0.2X SSC/1% SDS for 10 minutes). A restricted library of *K. lactis* genomic DNA (KpnI–BglII restriction fragments of between 1 and 1.5 kb in size) is then constructed according to Example E.1.3. and the restriction fragment hybridizing with the probe is cloned between the KpnI and BamHI sites of the vector pIC-20H, which generates the plasmid pYG1231 (FIG. 6, panel B). The genomic insert of this plasmid is then sequenced using the oligodeoxynucleotide Sq2101 (5'-GACCTATGGGGTAAGGATTAC-3') (SEQ ID NO. 11) as primer. This oligodeoxynucleotide corresponds to a nucleotide sequence present in the BglII–EcoRI fragment of the plasmid pYG1224 and located at about 30 nucleotides from the EcoRI site. It therefore makes it possible to determine the nucleotide sequence situated in 3' of this restriction site, and especially the sequence located between the EcoRI site and the translational stop codon of the messenger RNA corresponding to the *K. lactis* PRB1 gene.

E.1.6. Cloning of the 5' part of the gene.

The nucleotide sequence produced in E.1.5. demonstrates the existence of a HindIII restriction site located between the EcoRI site and the translational stop codon. The use of the KpnI–EcoRI restriction fragment corresponding to the C-terminal part of the *K. lactis* PRB1 gene as radioactive probe on the *K. lactis* genomic DNA digested with HindIII and a second enzyme makes it possible to identify, by Southern blotting, a HindIII–EcoRV fragment of about 1.7 kb which hybridizes with this probe. This restriction fragment is first cloned between the EcoRV and HindIII sites of the vector pIC-20R, thereby generating the plasmid pYG1237. A restriction map of the genomic DNA insert contained in the plasmid pYG1237 is produced (FIG. 6, panel C), and the following plasmids are generated: pYG1238 (plasmid pYG1237 deleted in relation to its PstI fragment), pYG1239 (PstI fragment of pYG1237 in the vector pUC19), pYG1240 (plasmid pYG1237 deleted in relation to its KpnI fragment), pYG1241 (plasmid pYG1237 deleted in relation to its ClaI fragment) and pYG1242 (plasmid pYG1237 deleted in relation to its SalI fragment; FIG. 6, panel C). The genomic inserts of these various plasmids are then sequenced with the aid of universal primers and the oligodeoxynucleotide Sq2148 (5'-GCTTCGGCAACATATTCG-3') (SEQ ID NO. 12) which makes it possible to sequence the region situated immediately in 5' of the BglII site. This strategy makes it possible to obtain overlapping sequences demonstrating the uniqueness of the BglII, ClaI and PstI restriction sites and making it possible to identify the probable ATG for initiation of translation of the *K. lactis* PRB1 gene.

E.1.7. Nucleotide sequence of the *K. lactis* PRB1 gene.

The compilation of the sequences determined in E.1.4., E.1.5 and E.1.6. covers the entire coding phase of the *K. lactis* PRB1 gens (FIG. 6, panel D). This sequence is given SEQ ID No. 1 and encodes a protein of 561 residues corresponding to the *K. lactis* protease B.

Example 2

CLONING OF *K. LACTIS* CARBOXYPEPTIDASE Y GENE

The general strategy described in Example 1 is repeated for the cloning of the carboxypeptidase Y gene of *K. lactis* CBS 2359/152.

E.2.1. Preparation of the probe.

A preparation of genomic DNA of the strain *S. cerevisiae* S288C [Mortimer and Johnston, Genetics 113 (1986) 35] is first carried out according to Example E.1.2. A PCR amplification of this genomic DNA preparation is then carried out with the oligonucleotides 5'-CTTCTTGGAGTT GTTCTTCG-3' and 5'-TGGCAAGACATCC GTCCACGCCTTATT-ACC-3', Specific for the PRC1 gene. An amplified fragment of the expected size (699 bp) is thus obtained which corresponds to positions 696–1395 (the ATG initiation codon being numbered +1) of the open reading frame of the S. Cerevisiae PRC1 gens [Valls et al., Cell 48 (1987) 887]. This fragment is then purified by electroelution and radiolabelled according to the "Random Priming" technique.

E.2.2. Cloning of the K. lactis PRC1 gene.

Figure 7:
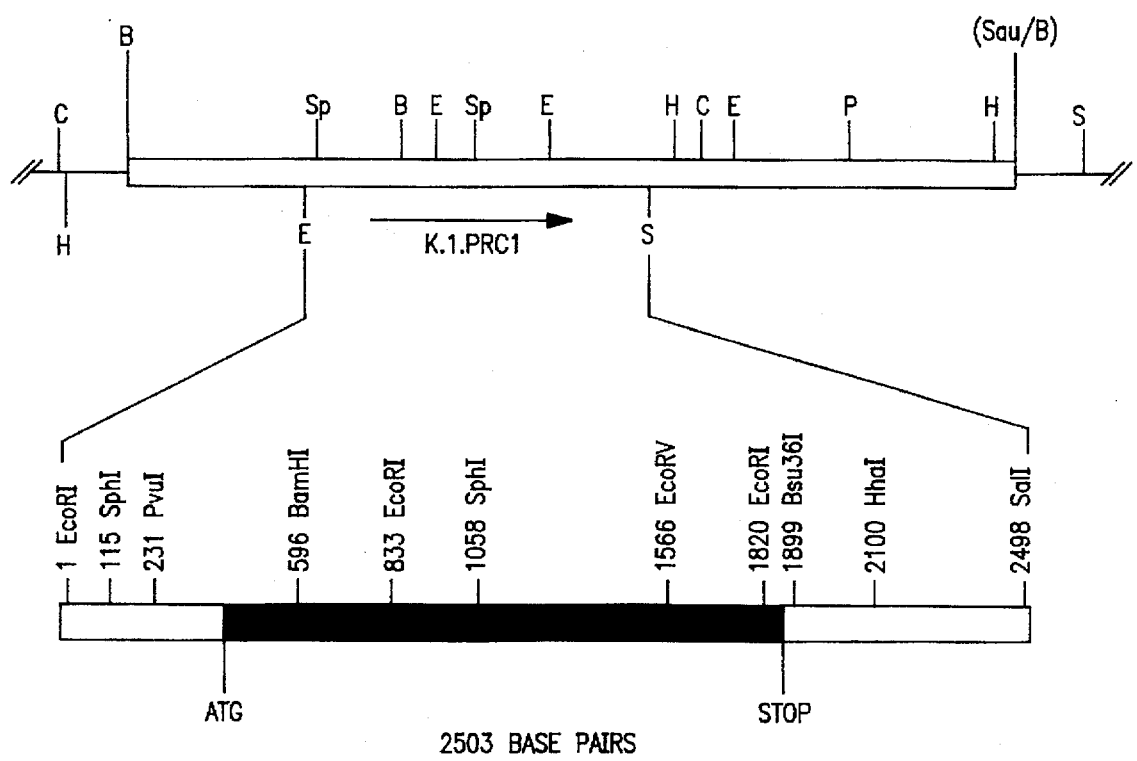
FIG. 7: Restriction map of the insert of the plasmid pC34. The box corresponds to the K. lactis genomic insert and the line corresponds to the sequences of the vector KEp6. The arrow indicates the position of the K. lactis PRC1 gene. The detailed part between the EcoRI and SalI sites corresponds to the sequenced region presented in SEQ ID NO 3. List of abbreviations: C=ClaI; H=HindIII; B=BamHI; E=EcoRI; P=PstI; S=SalI; Sp=SphI; Sau=Sau3A.

The K. lactis PRC1 gene is obtained by screening the K. lactis genomic library constructed Wésolowski-Louvel [Yeast A (1988) 71] from the strain 2359/152 in the cloning vector KEp6 [Chen et al., J. Basic. Microbiol. 28 (1988) 211]. The strain E. coli JM101 is transformed with the DNA from the library and the transformants are plated on LB medium supplemented with ampicillin (50 mg/l). 15,000 clones are then transferred onto nitrocellulose filters and the filters are hybridized with the probe described in Example E.2.1. The hybridization and washing conditions are those of Example E.1.3. 12 positive clones are thus isolated and one of them, designated pC34, is selected for the rest of the study. In a first instance, the hybridization of the plasmid pC34 with the probe corresponding to the S. cerevisiae PRC1 gene is confirmed by Southern blotting. A restriction map of the genomic insert (about 6.9 kb)of the plasmid pC34 is given in FIG. 7. The sequence of the 2.5 kb EcoRI–SalI fragment comprising the K. lactis PRC1 gene is then determined on the 2 strands. This sequence is presented SEQ ID No. 3.

Example 3

CLONING OF THE K. LACTIS PROTEASE A GENE

The general strategy described in the preceding examples is repeated for the cloning of the protease A gene from K. lactis CBS 2359/152.

E.3.1. Preparation of the probe.

An inner fragment of 449 bp of the PRA1 gene (or PEP4 gene) from S. cerevisiae is first amplified by the PCR technique starting with the plasmid CBZIB1 [Woolford et al., Mol. Cell. Biol. 6 (1986) 2500] provided by Dr E. Jones (Carnegie-Mellon University, Pittsburgh, Pa., USA) and the oligodeoxynucleotides 5'-CTGTTGATAAGGTGGTCC-3' (SEQ ID NO. 15) and 5'CAAGCGTGTAATCGTATGGC-3' (SEQ ID NO. 16). The amplified fragment obtained corresponds to positions 617–1066 of the open reading frame of the S. cerevisiae PRA1 gene, the ATG initiation codon being numbered +1. This fragment is then purified by electroelution and radiolabelled according to the "Random Priming" technique.

E.3.2. Cloning of the K. lactis PRA1 gene.

Figure 8:
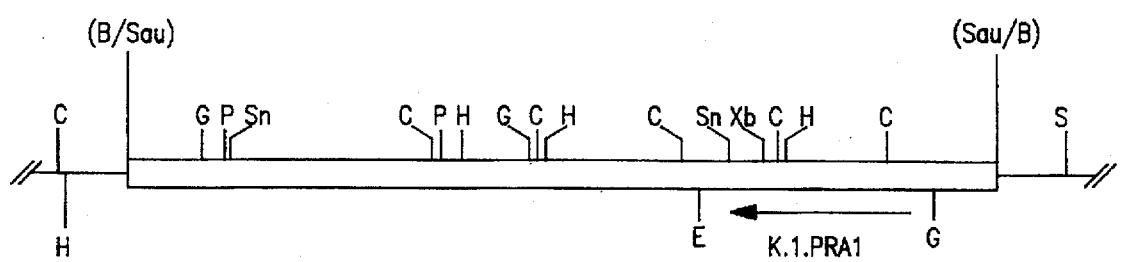
FIG. 8: Restriction map of the insert of the plasmid pA25/1. The box corresponds to the K. lactis genomic insert and the line corresponds to the sequences of the vector KEp6. The arrow indicates the rough position of the PRA1 gene as indicated by a Southern blot hybridization by means of specific 3' and 5' probes. List of abbreviations: C=ClaI; H=HindIII; B=BamHI; Sau=Sau3A; S=SalI; P=PstI; G=BglII; Xb=XbaI; Sn=SnaBI; E=EcoRI.

The PRA1 gene is obtained by screening the K. lactis genomic library constructed by Wéselowski-Louvel [Yeast 4 (1988) 71] starting with the strain 2359/152 in the cloning vector KEp6 [Chen et al., J. Basic Microbiol. 28 (1988) 211]. After transforming the library in E. coli JM101 and selecting in the presence of amplcillin (50 mg/l), 15,000 clones are then transferred onto nitrocellulose filters and the filters are hybridized with the probe described in Example E.3.1. The hybridization and washing conditions are those of Example E.1.3. Only 1 positive clone was thus isolated and designated pA25/1. In a first instance, the hybridization of the plasmid pA25/1 with the probe corresponding to the S. cerevisiae PRA1 gene is confirmed by Southern blotting. A restriction map of the genomic insert (about 7.5 kb) of this plasmid is represented in FIG. 8. The sequence of the 1.6 kb ClaI–EcoRI fragment comprising the K. lactis PRA1 gene is then determined on the 2 strands. This sequence is presented SEQ ID No. 5.

Example 4

TRANSFORMATION OF THE YEASTS

The transformation of the yeasts belonging to the genus Kluyveromyces, and in particular the strains K. lactis MW98-8C, CBS 293.91 and CBS 294.91 (uraA) is carried out for example by the technique for treating whole cells with lithium acetate [Ito H. et al., J. Bacteriol. 153 (1983) 163–168], modified as follows. The growth of the cells occurs at 28° C. in 50 ml of YPD medium, with stirring and up to an optical density of 600 nm (OD600) of between 0.6 and 0.8; the cells are then harvested by low-speed centrifugation, washed in a sterile solution of TE (10 mMTris HCl pH 7.4; 1 mM EDTA), resuspended in 3–4 ml of lithium acetate (0.1 M in TE) in order to obtain a cell density of about $2 \times 10^8$ cells/ml, and then incubated at 30° C. for 1 hour with gentle stirring. 0.1 ml aliquots of the resulting suspension of competent cells are incubated at 30° C. for 1 hour in the presence of DNA and at a final concentration of 35% polyethylene glycol ($PEG_{4000}$, Sigma). After a heat shock of 5 minutes at 42° C., the cells are washed twice, then resuspended in 0.2 ml sterile water. In the case or the selectable marker is the S. cerevisiae URA3 gene, the cells are directly plated on YNB (Yeast Nitrogen Base; Difco)/glucose (20 g/l)/agar. In the case or the selectable marker is the aph gene of the transposon Tn903, the cells are first incubated for 16 hours at 28° C. in 2 ml of YPD medium so as to allow the phenotypic expression of the G418 resistance gene expressed under the control of the $P_{k1}$ promoter (cf. EP 361 991); 200 μl of the cellular suspension are then plated on selective YPD dishes (G418, 200 μg/ml). The dishes are incubated at 28° C. and the disruptants or the transformants appear after 2 to 3 days of cell growth.

Example 5

DISRUPTION OF PROTEASE GENES IN K. LACTIS

E.5.1. K. lactis strains disrupted for the PRB1 gene.

Figure 9A:
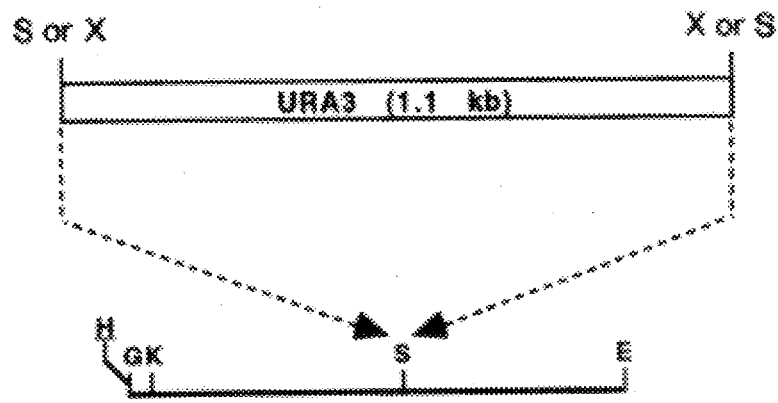
FIGS. 9A and B: Panel A: Restriction map of the HindIII-EcoRI restriction fragment of the plasmid pYG1232. The position of the cleavage sites of the following endonucleases is indicated: G=BglII; S=SalI; E=EcoRI; H=HindIII.
Figure 9B:
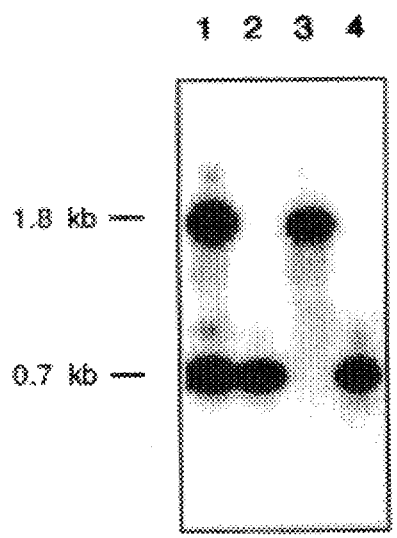
Figure 10A:
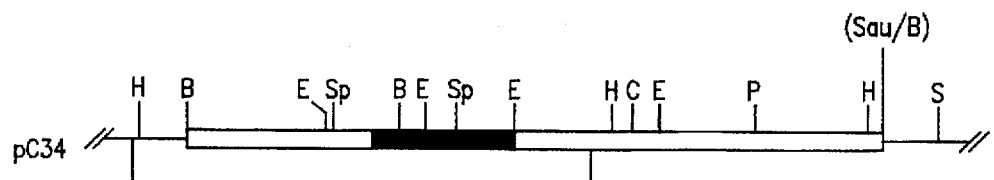
Figure 10B:
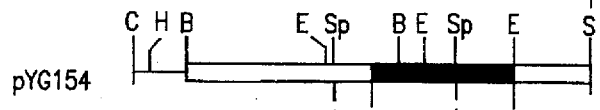
Figure 10C:
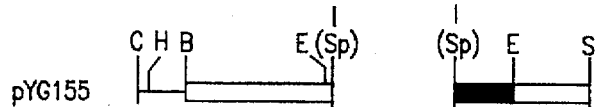
Figure 10D:
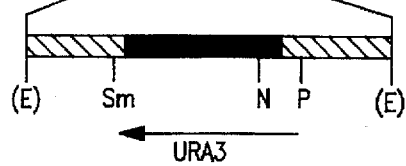
Figure 10D:

The plasmid pYG1229 is constructed by cloning the HindIII–EcoRI fragment (including the BglII–EcoRI fragment of about 700 bp and corresponding to the C-terminal part of the K. Lactis PRB1 gene) of the plasmid pYG1224 between the corresponding sites of the plasmid pUC9. The plasmid pYG1228 is constructed by cloning the HindIII fragment of 1.1 kb and corresponding to the S. cerevisiae URA3 gens derived from the plasmid pCG3 [Gerbaud et al., Curt. Genetics A (1981) 173] in the HindIII site of the plasmid pIC-20R. The plasmid pYG1228 therefore makes it possible to have a SalI–XhoI restriction fragment of about 1.1 kb and containing the entire HindIII fragment containing the S. cerevisiae URA3 gens. This restriction fragment is then cloned into the SalI site of the plasmid pYG1229 which generates the plasmid pYG1232 (2 possible orientations). The digestion of this plasmid with the BglII and EcoRI enzymes makes it possible to generate a restriction fragment of about 1.8 kb corresponding to the S. Cerevisiae URA3 gene bordered by K. lactis genomic sequences derived from the PRB1 gene (FIG. 9, panel A). The transformation of the K. lactis uraA mutants with the BglII–EcoRI fragment of the plasmid pYG1232 generates transformed clones (complemented by the S. cerevisiae URA3 gens) corresponding to the integration of this fragment in to the chromosome. Panel B of FIG. 9 shows the integration of this fragment into the genomic DNA of the *K. lactis* CBS 294.91 strain (uraA) after non-homologous recombination (well 1) or after homologous recombination in the PRB1 gene (well 3, this disruptant is noted Y750). The disruption of the wild-type allel of the PRB1 gene does not modify the growth characteristics of the strain.

E.5.2. *K. lactis* strains disrupted for the PRC1 gene.

The 4.4 kb SalI–SphI fragment derived from the plasmid pC34 is first subcloned into the corresponding sites of the vector pIC-20R, which generates the plasmid pYG154 (FIG. 12, panel b). This plasmid is then digested with the SphI enzyme, then treated with phage T4 DNA polymerase I in the presence of calf intestinal phosphatase (CIP). The plasmid obtained is then ligated to the EcoRI fragment of 1.6 kb carrying the *S. cerevisiae* URA3 gene derived from the plasmid pKan707 (EP 361 991), previously treated with the Klenow fragment of DNA polymerase I of *E. coli*. The plasmid obtained is designated pYG155 (FIG. 10, panel c). The 4.5 kb SalI–BamHI fragment of the plasmid pYG155 is then purified by electroelution and used to transform the *K. lactis* CBS 294.91 strain (uraA). The transformants are selected for the Ura$^+$ phenotype and a few clones are then analysed by Southern blotting in order to check the site of integration of the URA3 marker. The clone Y797 is thus identified in which the chromosomal PRC1 gene has been replaced, by homologous recombination, by the disrupted allel constructed in vitro. The disruption of the wild-type allele of the PRC1 gene does not modify the growth characteristics of the strain.

Example 6

EXPRESSION PLASMIDS

E.6.1. Plasmid pYG1212.

The genes for the proteins of interest which it is desired to secrete and/or express are first inserted, "in the productive orientation" (defined as the orientation which places the N-terminal region of the protein proximally relative to the transcription promoter), under the control of regulatable or constitutive functional promoters such as for example those present in the plasmids pYG105 (K- lactis LAC4 promoter), pYG106 (*S. cerevisiae* PGK promoter), pYG536 (*S. cerevisiae* PHO5 promoter), or hybrid promoters such as those described in patent application EP 361 991. The plasmids pYG105 and pYG106 are particularly useful because they allow the expression of genes included in HindIII restriction fragments from regulatable (pYG105) or constitutive (pYG106) promoters which are functional in *K. lactis*.

The plasmid pYG105 corresponds to the plasmid pKan707 described in patent application EP 361 991 in which the unique HindIII restriction site located in the gene for resistance to geneticin (G418) has been destroyed by site-directed mutagenesis, conserving a protein unchanged (oligodeoxynucleotide 5'GAAATGCATAAGCT CTTGCCATTCTCACCG-3') (SEQ ID NO. 17). The SalI–SacI fragment encoding the URA3 gene of the plasmid thus mutated was then replaced by a SaiI-Sac1 restriction fragment containing an expression cassette consisting of the *K. lactis* LAC4 promoter [in the form of a SalI–HindIII fragment derived from the plasmid pYG1075 Fleer et al., Bio/Technology 9 (1991) 968]) and the *S. cerevisiae* PGK gene terminator [in the form of a HindIII–SacI fragment; Fleer et al., Bio/Technology 9 (1991) 968]. The plasmid pYG105 is mitotically very stable in Kluyveromyces yeasts and a restriction map is given in FIG. 11. The plasmids pYG105 and pYG106 differ from each other only in the nature of the transcription promoter encoded by the SalI–HindIII fragment.

The protein encoded by the plasmid pYG1212 corresponds approximately to the first two domains of human serum albumin (HSA). This molecular variant, obtained by digestion of the C-terminal end of HSA using exonuclease Ba131 from the unique MstII site located 3 amino acids from the C-terminal end of HSA, is derived from the plasmid YP40 described in patent application EP 413 622. Briefly, the HindIII–MstII restriction fragment of the plasmid YP40, corresponding to residues 1 to 403 of HSA (the ATG for initiation of translation is noted +1), is ligated to the MstII–HindIII fragment of the plasmid pYG221 [Yeh et al., Proc. Natl. Acad. Sci. USA 89 (1992) 1904], which generates a HindIII fragment including the 403 N-terminal residues of HSA followed by the last three residues of HSA (residues Leu-Gly-Leu) and a translational stop codon [truncated variant noted HSA$_{(1-403)}$]. The HindIII fragment is then cloned in the productive orientation into the plasmid pYG105, which generates the plasmid pYG1212 (FIG. 11).

Example 7

SECRETION POTENTIAL OF THE DISRUPTANTS

E.7.1. HSA$_{(1-403)}$ in a disruptant for protease B.

In a first stage, the yeasts *K. Lactis* CBS 293.91 and Y750 are transformed with the plasmid pYG1212. After selection on rich medium supplemented with G418, the recombinant clones are tested for their capacity to secrete the protein HSA$_{(1-403)}$. A few clones are incubated in YPD or YPL medium at 28° C. The culture supernatents are recovered by centrifugation when the cells reach the stationary growth phase, concentrated 10 fold by precipitation for 30 minutes at −20° C. in a final concentration of 60% ethanol, then tested after electrophoresis on an 8.5% SDS-PAGE gel and staining of the gel with coomassie blue. The results presented in FIG. 12 demonstrate that the disruptant Y750 (prb1°) secretes quantities of protein which are much higher than the quantities secreted by its non-disrupted homologue. This is true after 2, 4 or 7 days of growth, independently of the carbon source used (glucose or lactose).

---

We claim:

1. A Kluyverornyces yeast comprising a genetic modification in its PRA1, PRB1 or PRC1 gini, wherein said modification results in loss of protease activity encoded by said gene.

2. The Kluyverormyces yeast according to claim 1, wherein the modification is in
   a) protein coding region of said gene;
   b) a region responsible for transcriptional regulation of said gene; or
   c) both a protein coding region of said gene and a region responsible for transcriptional regulation of said gene.

3. The Kluyveromyces yeast according to claim 1, selected from the group consisting of K. lactis, K. fragilis, K, drosophilarum, and K. waltii.

4. A process for preparing the Kluyveromyces yeast of claim 1 comprising replacing all or part of said gene with a modified version thereof.

5. A Kluyveromyces yeast comprising
   a genetic modification in its PRA1, PRB1, or PRC1 gene, wherein said modification results in loss of protease activity encoded by said gene, and
   an exogenous DNA sequence encoding at least one protein.

6. The Kluyveromyces yeast according to claim 5, wherein the exogenous DNA sequence further comprises a region for initiation of transcription and translation operably linked to the sequence encoding the protein.

7. The Kluyveromyces yeast according to claim 5, wherein the exogenous sequence comprises a region encoding an exporting sequence for secretion of the protein.

8. The Kluyveromyces yeast according to claim 5, wherein the exogenous DNA sequence is part of an autonomously replicating vector or is integrated into a chromosome.

9. A process for producing recombinant proteins comprising culturing the Kluyverornyces yeast of claim 5 under conditions for expression of said exogenous DNA sequence.

10. A process for producing recombinant proteins comprising culturing the Kluyveromyces yeast of claim 6 under conditions for expression of said exogenous DNA sequence.

11. A process for producing recombinant proteins comprising culturing the Kluyverormyces yeast of claim 7 under conditions for expression of said exogenous DNA sequence.

12. The Kluyveromyces yeast according to claim 5, wherein the exogenous DNA sequence encodes a protein of pharmaceutical interest.

13. A process for producing recombinant proteins comprising culturing the Kluyveromyces yeast of claim 12 under conditions for expression of said exogenous DNA sequence.

* * * * *

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
        ( A ) LENGTH: 1685 base pairs (B) TYPE: nucleic acid
(C) STRANDEDNESS: double
(D) TOPOLOGY: linear (ii) MOLECULE TYPE: cDNA (vi) ORIGINAL SOURCE:
(A) ORGANISM: Kluyveromyces lactis (ix) FEATURE:
(A) NAME/KEY: CDS
(B) LOCATION: 1..1683
(D) OTHER INFORMATION: /product="Protease B gene"
/ gene="K1.PRB1"

(xi) SEQUENCE DESCRIPTION: SEQ ID NO:1:

| ATG | AAG | TTC | GAA | AAT | ACA | TTA | TTG | ACT | ATA | ACC | GCA | TTG | TCT | ACC | GTG | 48 |
| Met | Lys | Phe | Glu | Asn | Thr | Leu | Leu | Thr | Ile | Thr | Ala | Leu | Ser | Thr | Val | |
| 1 | | | | 5 | | | | | 10 | | | | | 15 | | |

| GCT | ACT | GCT | TTG | GTT | ATC | CCT | GAA | GTT | AAT | AGG | GAA | AAC | AAG | CAT | GGT | 96 |
| Ala | Thr | Ala | Leu | Val | Ile | Pro | Glu | Val | Asn | Arg | Glu | Asn | Lys | His | Gly | |
| | | | 20 | | | | | 25 | | | | | 30 | | | |

| GAC | AAG | AGC | GTT | GCC | ATC | AAA | GAT | CAT | GCT | TCT | TCT | GAT | TTG | GAT | AAG | 144 |
| Asp | Lys | Ser | Val | Ala | Ile | Lys | Asp | His | Ala | Ser | Ser | Asp | Leu | Asp | Lys | |
| | | 35 | | | | | 40 | | | | | 45 | | | | |

| CCT | CAA | CAT | CAT | GCT | AAT | GGC | AAG | GCT | CGT | TCT | AAG | TCT | CGT | GGT | CGC | 192 |
| Pro | Gln | His | His | Ala | Asn | Gly | Lys | Ala | Arg | Ser | Lys | Ser | Arg | Gly | Arg | |
| 50 | | | | | 55 | | | | | 60 | | | | | | |

| TGC | GCA | GAC | TCC | AAG | AAA | TTC | GAC | AAG | CTA | CGT | CCA | GTC | GAC | GAT | GCT | 240 |
| Cys | Ala | Asp | Ser | Lys | Lys | Phe | Asp | Lys | Leu | Arg | Pro | Val | Asp | Asp | Ala | |
| 65 | | | | 70 | | | | | 75 | | | | | 80 | | |

| TCA | GCT | ATT | TTA | GCT | CCA | CTT | TCT | ACA | GTT | AAT | GAT | ATT | GCC | AAC | AAG | 288 |
| Ser | Ala | Ile | Leu | Ala | Pro | Leu | Ser | Thr | Val | Asn | Asp | Ile | Ala | Asn | Lys | |
| | | | | 85 | | | | | 90 | | | | | 95 | | |

| ATT | CCT | AAT | CGT | TAC | ATC | ATT | GTC | TTT | AAG | AAA | GAT | GCC | TCT | GCA | GAT | 336 |
| Ile | Pro | Asn | Arg | Tyr | Ile | Ile | Val | Phe | Lys | Lys | Asp | Ala | Ser | Ala | Asp | |
| | | | 100 | | | | | 105 | | | | | 110 | | | |

| GAA | GTG | AAG | TTC | CAT | CAA | GAA | CTA | GTC | TCT | GTC | GAA | CAT | GCC | AAG | GCA | 384 |
| Glu | Val | Lys | Phe | His | Gln | Glu | Leu | Val | Ser | Val | Glu | His | Ala | Lys | Ala | |
| | | 115 | | | | | 120 | | | | | 125 | | | | |

| CTA | GGT | TCC | TTA | GCT | GAC | CAT | GAC | CCA | TTC | TTC | ACA | GCA | ACT | TCC | GGT | 432 |
| Leu | Gly | Ser | Leu | Ala | Asp | His | Asp | Pro | Phe | Phe | Thr | Ala | Thr | Ser | Gly | |
| | 130 | | | | | 135 | | | | | 140 | | | | | |

| GAA | CAT | AGT | GAA | TTT | GGT | GTC | AAA | GCA | CAC | TCT | TTG | GAA | GGT | GGT | ATT | 480 |
| Glu | His | Ser | Glu | Phe | Gly | Val | Lys | Ala | His | Ser | Leu | Glu | Gly | Gly | Ile | |
| 145 | | | | | 150 | | | | | 155 | | | | | 160 | |

| CAA | GAC | TCT | TTT | GAT | ATT | GCC | GGT | TCC | CTT | TCT | GGT | TAT | GTT | GGC | TAC | 528 |
| Gln | Asp | Ser | Phe | Asp | Ile | Ala | Gly | Ser | Leu | Ser | Gly | Tyr | Val | Gly | Tyr | |
| | | | | 165 | | | | | 170 | | | | | 175 | | |

| TTC | ACA | AAA | GAA | GTT | ATC | GAT | TTC | ATC | AGA | AGA | AGC | CCA | TTG | GTT | GAA | 576 |
| Phe | Thr | Lys | Glu | Val | Ile | Asp | Phe | Ile | Arg | Arg | Ser | Pro | Leu | Val | Glu | |
| | | | 180 | | | | | 185 | | | | | 190 | | | |

| TTT | GTT | GAA | GAA | GAT | TCT | ATG | GTT | TTC | TCT | AAT | AGT | TTC | AAT | ACC | CAA | 624 |
| Phe | Val | Glu | Glu | Asp | Ser | Met | Val | Phe | Ser | Asn | Ser | Phe | Asn | Thr | Gln | |
| | | 195 | | | | | 200 | | | | | 205 | | | | |

| AAC | AGT | GCT | CCT | TGG | GGT | CTA | GCT | CGT | ATT | TCT | CAT | CGT | GAA | AAG | TTG | 672 |
| Asn | Ser | Ala | Pro | Trp | Gly | Leu | Ala | Arg | Ile | Ser | His | Arg | Glu | Lys | Leu | |
| | 210 | | | | | 215 | | | | | 220 | | | | | |

| AAT | TTA | GGA | TCT | TTC | AAC | AAG | TAC | TTG | TAT | GAT | GAT | GAC | GCT | GGT | AAA | 720 |
| Asn | Leu | Gly | Ser | Phe | Asn | Lys | Tyr | Leu | Tyr | Asp | Asp | Asp | Ala | Gly | Lys | |
| 225 | | | | | 230 | | | | | 235 | | | | | 240 | |

| GGT | GTT | ACT | GCT | TAC | GTT | GTT | GAC | ACT | GGT | GTC | AAT | GTC | AAC | CAT | AAG | 768 |
| Gly | Val | Thr | Ala | Tyr | Val | Val | Asp | Thr | Gly | Val | Asn | Val | Asn | His | Lys | |
| | | | | 245 | | | | | 250 | | | | | 255 | | |

| | | | | | | | | | | | | | | | | |
|---|---|---|---|---|---|---|---|---|---|---|---|---|---|---|---|---|
| GAC | TTT | GAT | GGC | AGA | GCT | GTT | TGG | GGT | AAG | ACT | ATT | CCA | AAA | GAT | GAT | 816 |
| Asp | Phe | Asp | Gly 260 | Arg | Ala | Val | Trp | Gly 265 | Lys | Thr | Ile | Pro | Lys 270 | Asp | Asp | |
| CCA | GAT | GTA | GAT | GGA | AAT | GGT | CAC | GGT | ACC | CAC | TGT | GCT | GGT | ACC | ATC | 864 |
| Pro | Asp | Val 275 | Asp | Gly | Asn | Gly | His 280 | Gly | Thr | His | Cys | Ala 285 | Gly | Thr | Ile | |
| GGT | TCG | GTT | CAT | TAT | GGT | GTT | GCT | AAG | AAT | GCT | GAT | ATA | GTT | GCC | GTT | 912 |
| Gly | Ser 290 | Val | His | Tyr | Gly | Val 295 | Ala | Lys | Asn | Ala | Asp 300 | Ile | Val | Ala | Val | |
| AAG | GTT | TTG | AGA | TCT | AAT | GGT | TCT | GGT | ACC | ATG | TCT | GAT | GTT | GTT | AAA | 960 |
| Lys 305 | Val | Leu | Arg | Ser | Asn 310 | Gly | Ser | Gly | Thr | Met 315 | Ser | Asp | Val | Val | Lys 320 | |
| GGT | GTC | GAA | TAT | GTT | GCC | GAA | GCA | CAC | AAG | AAA | GCT | GTT | GAA | GAA | CAA | 1008 |
| Gly | Val | Glu | Tyr | Val 325 | Ala | Glu | Ala | His | Lys 330 | Lys | Ala | Val | Glu | Glu 335 | Gln | |
| AAG | AAA | GGG | TTC | AAG | GGT | TCA | ACT | GCT | AAC | ATG | TCT | TTG | GGT | GGT | GGT | 1056 |
| Lys | Lys | Gly | Phe 340 | Lys | Gly | Ser | Thr | Ala 345 | Asn | Met | Ser | Leu | Gly 350 | Gly | Gly | |
| AAA | TCT | CCA | GCC | TTG | GAT | TTG | GCC | GTC | AAC | GCC | GCT | GTT | AAG | GCA | GGT | 1104 |
| Lys | Ser | Pro 355 | Ala | Leu | Asp | Leu | Ala 360 | Val | Asn | Ala | Ala | Val 365 | Lys | Ala | Gly | |
| GTT | CAT | TTT | GCT | GTT | GCT | GCC | GGT | AAT | GAG | AAC | CAA | GAT | GCT | TGT | AAC | 1152 |
| Val | His 370 | Phe | Ala | Val | Ala | Ala 375 | Gly | Asn | Glu | Asn | Gln 380 | Asp | Ala | Cys | Asn | |
| ACT | TCG | CCT | GCC | GCG | GCT | GAG | AAT | GCT | ATC | ACG | GTT | GGT | GCC | TCC | ACA | 1200 |
| Thr 385 | Ser | Pro | Ala | Ala | Ala 390 | Glu | Asn | Ala | Ile | Thr 395 | Val | Gly | Ala | Ser | Thr 400 | |
| TTA | AGT | GAT | GAA | AGA | GCT | TAC | TTT | TCC | AAT | TGG | GGT | AAA | TGT | GTC | GAC | 1248 |
| Leu | Ser | Asp | Glu | Arg 405 | Ala | Tyr | Phe | Ser | Asn 410 | Trp | Gly | Lys | Cys | Val 415 | Asp | |
| ATC | TTT | GGT | CCG | GGT | TTG | AAT | ATC | TTA | TCT | ACC | TAC | ATT | GGT | TCT | GAT | 1296 |
| Ile | Phe | Gly | Pro 420 | Gly | Leu | Asn | Ile | Leu 425 | Ser | Thr | Tyr | Ile | Gly 430 | Ser | Asp | |
| ACT | GCT | ACT | GCT | ACC | TTG | TCT | GGT | ACT | TCT | ATG | GCC | ACT | CCT | CAT | GTT | 1344 |
| Thr | Ala | Thr 435 | Ala | Thr | Leu | Ser | Gly 440 | Thr | Ser | Met | Ala | Thr 445 | Pro | His | Val | |
| GTC | GGT | TTG | CTA | ACA | TAT | TTC | TTG | TCC | TTG | CAA | CCA | GAT | GCT | GAT | AGT | 1392 |
| Val | Gly | Leu 450 | Leu | Thr | Tyr | Phe | Leu 455 | Ser | Leu | Gln | Pro | Asp 460 | Ala | Asp | Ser | |
| GAA | TAT | TTC | CAT | GCC | GCT | GGC | GGT | ATT | ACT | CCT | TCC | CAA | CTC | AAG | AAG | 1440 |
| Glu 465 | Tyr | Phe | His | Ala | Ala 470 | Gly | Gly | Ile | Thr | Pro 475 | Ser | Gln | Leu | Lys | Lys 480 | |
| AAG | TTA | ATT | GAT | TTC | TCT | ACT | AAG | AAC | GTA | TTG | TCC | GAT | CTA | CCT | GAA | 1488 |
| Lys | Leu | Ile | Asp | Phe 485 | Ser | Thr | Lys | Asn | Val 490 | Leu | Ser | Asp | Leu | Pro 495 | Glu | |
| GAT | ACC | GTG | AAC | TAC | TTG | ATT | TAC | AAC | GGT | GGT | GGT | CAA | GAT | TTG | GAT | 1536 |
| Asp | Thr | Val | Asn 500 | Tyr | Leu | Ile | Tyr | Asn 505 | Gly | Gly | Gly | Gln | Asp 510 | Leu | Asp | |
| GAC | CTA | TGG | GGT | AAG | GAT | TAC | TCT | ATT | GGA | AAA | GAA | CCA | TCT | GCC | AAC | 1584 |
| Asp | Leu | Trp 515 | Gly | Lys | Asp | Tyr | Ser 520 | Ile | Gly | Lys | Glu | Pro 525 | Ser | Ala | Asn | |
| CCT | GAA | TTC | AGC | TTG | GAA | AGC | TTG | ATT | AAC | TCT | TTG | GAT | TCA | AAG | ACT | 1632 |
| Pro | Glu | Phe 530 | Ser | Leu | Glu | Ser | Leu 535 | Ile | Asn | Ser | Leu | Asp 540 | Ser | Lys | Thr | |
| GAT | GCT | ATC | TTT | GAC | GAC | GTT | AGA | CAG | TTG | TTG | GAC | CAA | TTT | AAT | ATC | 1680 |
| Asp | Ala | Ile | Phe 545 | Asp | Asp | Val | Arg | Gln 550 | Leu | Leu | Asp | Gln | Phe 555 | Asn | Ile 560 | |
| ATC | TA | | | | | | | | | | | | | | | 1685 |
| Ile | | | | | | | | | | | | | | | | |

( 2 ) INFORMATION FOR SEQ ID NO:2:

( i ) SEQUENCE CHARACTERISTICS:
        ( A ) LENGTH: 561 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Lys Phe Glu Asn Thr Leu Leu Thr Ile Thr Ala Leu Ser Thr Val
 1               5                  10                  15

Ala Thr Ala Leu Val Ile Pro Glu Val Asn Arg Glu Asn Lys His Gly
            20                  25                  30

Asp Lys Ser Val Ala Ile Lys Asp His Ala Ser Ser Asp Leu Asp Lys
        35                  40                  45

Pro Gln His His Ala Asn Gly Lys Ala Arg Ser Lys Ser Arg Gly Arg
    50                  55                  60

Cys Ala Asp Ser Lys Lys Phe Asp Lys Leu Arg Pro Val Asp Asp Ala
65                  70                  75                  80

Ser Ala Ile Leu Ala Pro Leu Ser Thr Val Asn Asp Ile Ala Asn Lys
                85                  90                  95

Ile Pro Asn Arg Tyr Ile Ile Val Phe Lys Lys Asp Ala Ser Ala Asp
            100                 105                 110

Glu Val Lys Phe His Gln Glu Leu Val Ser Val Glu His Ala Lys Ala
        115                 120                 125

Leu Gly Ser Leu Ala Asp His Asp Pro Phe Phe Thr Ala Thr Ser Gly
    130                 135                 140

Glu His Ser Glu Phe Gly Val Lys Ala His Ser Leu Glu Gly Gly Ile
145                 150                 155                 160

Gln Asp Ser Phe Asp Ile Ala Gly Ser Leu Ser Gly Tyr Val Gly Tyr
                165                 170                 175

Phe Thr Lys Glu Val Ile Asp Phe Ile Arg Arg Ser Pro Leu Val Glu
            180                 185                 190

Phe Val Glu Glu Asp Ser Met Val Phe Ser Asn Ser Phe Asn Thr Gln
        195                 200                 205

Asn Ser Ala Pro Trp Gly Leu Ala Arg Ile Ser His Arg Glu Lys Leu
    210                 215                 220

Asn Leu Gly Ser Phe Asn Lys Tyr Leu Tyr Asp Asp Ala Gly Lys
225                 230                 235                 240

Gly Val Thr Ala Tyr Val Val Asp Thr Gly Val Asn Val Asn His Lys
                245                 250                 255

Asp Phe Asp Gly Arg Ala Val Trp Gly Lys Thr Ile Pro Lys Asp Asp
            260                 265                 270

Pro Asp Val Asp Gly Asn Gly His Gly Thr His Cys Ala Gly Thr Ile
        275                 280                 285

Gly Ser Val His Tyr Gly Val Ala Lys Asn Ala Asp Ile Val Ala Val
    290                 295                 300

Lys Val Leu Arg Ser Asn Gly Ser Gly Thr Met Ser Asp Val Val Lys
305                 310                 315                 320

Gly Val Glu Tyr Val Ala Glu Ala His Lys Lys Ala Val Glu Glu Gln
                325                 330                 335

Lys Lys Gly Phe Lys Gly Ser Thr Ala Asn Met Ser Leu Gly Gly Gly
            340                 345                 350

Lys Ser Pro Ala Leu Asp Leu Ala Val Asn Ala Ala Val Lys Ala Gly
        355                 360                 365
```

-continued

| | | | | | | | | | | | | | | |
|---|---|---|---|---|---|---|---|---|---|---|---|---|---|---|
| Val | His 370 | Phe | Ala | Val | Ala 375 | Ala | Gly | Asn | Glu | Asn 380 | Gln | Asp | Ala | Cys | Asn |
| Thr 385 | Ser | Pro | Ala | Ala 390 | Ala | Glu | Asn | Ala | Ile | Thr 395 | Val | Gly | Ala | Ser | Thr 400 |
| Leu | Ser | Asp | Glu | Arg 405 | Ala | Tyr | Phe | Ser | Asn 410 | Trp | Gly | Lys | Cys | Val 415 | Asp |
| Ile | Phe | Gly | Pro 420 | Gly | Leu | Asn | Ile | Leu 425 | Ser | Thr | Tyr | Ile | Gly 430 | Ser | Asp |
| Thr | Ala | Thr 435 | Ala | Thr | Leu | Ser | Gly 440 | Thr | Ser | Met | Ala | Thr 445 | Pro | His | Val |
| Val | Gly 450 | Leu | Leu | Thr | Tyr | Phe 455 | Leu | Ser | Leu | Gln | Pro 460 | Asp | Ala | Asp | Ser |
| Glu 465 | Tyr | Phe | His | Ala | Ala 470 | Gly | Gly | Ile | Thr | Pro 475 | Ser | Gln | Leu | Lys | Lys 480 |
| Lys | Leu | Ile | Asp | Phe 485 | Ser | Thr | Lys | Asn | Val 490 | Leu | Ser | Asp | Leu | Pro 495 | Glu |
| Asp | Thr | Val | Asn 500 | Tyr | Leu | Ile | Tyr | Asn 505 | Gly | Gly | Gly | Gln | Asp 510 | Leu | Asp |
| Asp | Leu | Trp 515 | Gly | Lys | Asp | Tyr | Ser 520 | Ile | Gly | Lys | Glu | Pro 525 | Ser | Ala | Asn |
| Pro | Glu 530 | Phe | Ser | Leu | Glu | Ser 535 | Leu | Ile | Asn | Ser | Leu 540 | Asp | Ser | Lys | Thr |
| Asp 545 | Ala | Ile | Phe | Asp | Asp 550 | Val | Arg | Gln | Leu | Leu 555 | Asp | Gln | Phe | Asn | Ile 560 |
| Ile | | | | | | | | | | | | | | | |

( 2 ) INFORMATION FOR SEQ ID NO:3:

( i ) SEQUENCE CHARACTERISTICS:
        ( A ) LENGTH: 2503 base pairs
        ( B ) TYPE: nucleic acid
        ( C ) STRANDEDNESS: double
        ( D ) TOPOLOGY: linear ( i i ) MOLECULE TYPE: cDNA ( v i ) ORIGINAL SOURCE:
        ( A ) ORGANISM: Kluyveromyces lactis ( i x ) FEATURE:
        ( A ) NAME/KEY: CDS
        ( B ) LOCATION: 387..1862
        ( D ) OTHER INFORMATION: /product="K. lactis protease C
            gene"
        / gene="Kl.PRC1"

( x i ) SEQUENCE DESCRIPTION: SEQ ID NO:3:

| | | | | | |
|---|---|---|---|---|---|
| GAATTCTGTC | AACTGGATAC | GGAAGACAAT | AGAATGGACA | CATAATGGTC | TCAATACGAC | 60 |
| AATTCAACGG | CTCTTAGAAG | GTGAGTTATT | CTTGACATTT | TCATGGCTCT | TCGAGCATGC | 120 |
| TTTCTAAGAT | GACGCGGAAG | GTGAAAAAGA | TTAGAAAACG | GCCATTCACG | TGAATATCAC | 180 |
| GTGAACTACA | AATTCATGAT | ATATTACCGC | CAATAGTATT | GGTGGTTACC | CGATCGTATC | 240 |
| GAATGTACTG | ACTTCGAAAA | TATGAATAGT | CCTCTTTAAA | ACAAAGGGTT | TTCAGTGACC | 300 |
| CTTACTCCAT | CATCTCCTTA | GTATTTGGTC | TACAGACTCG | CCATTGCCGT | ATATTCAGGG | 360 |

| | | | | | | | |
|---|---|---|---|---|---|---|---|
| TAGTAGTCAG | TACATCGGTG | TCTGCC | ATG | GTT | TCG | ATA | AAG | TTT | CTT | TTA | TCT | 413 |
| | | | Met 1 | Val | Ser | Ile | Lys 5 | Phe | Leu | Leu | Ser | |

| | | | | | | | | | | | | | | | |
|---|---|---|---|---|---|---|---|---|---|---|---|---|---|---|---|
| TTA | TAC | GGC | TGG | CTA | TCT | GTC | ACT | TTA | GCC | ATC | TCG | TTG | AAT | GCC | GTT | 461 |
| Leu | Tyr | Gly | Trp | Leu | Ser | Val | Thr | Leu | Ala | Ile | Ser | Leu | Asn | Ala | Val | |

| | | | | | | | | | | | | | | | | |
|---|---|---|---|---|---|---|---|---|---|---|---|---|---|---|---|---|
| GTT | GAT | AGT | TTA | TTC | TCG | AAC | AGT | TTC | GAC | GGG | AAT | AAC | AAC | ATC | GAG | 509 |
| Val | Asp | Ser | Leu | Phe | Ser | Asn | Ser | Phe | Asp | Gly | Asn | Asn | Asn | Ile | Glu | |
| | | | 30 | | | | | 35 | | | | | 40 | | | |
| GAT | CAT | GAA | ACT | GCA | AAT | TAT | AAC | ACT | CAG | TTT | AGT | GTC | TTC | AGC | TCA | 557 |
| Asp | His | Glu | Thr | Ala | Asn | Tyr | Asn | Thr | Gln | Phe | Ser | Val | Phe | Ser | Ser | |
| | | | 45 | | | | | 50 | | | | | 55 | | | |
| AAT | ATT | GAC | GAC | GCT | TAT | TCA | TTG | AGA | ATT | AAA | CCT | TTG | GAT | CCC | AAA | 605 |
| Asn | Ile | Asp | Asp | Ala | Tyr | Ser | Leu | Arg | Ile | Lys | Pro | Leu | Asp | Pro | Lys | |
| | | 60 | | | | | 65 | | | | | 70 | | | | |
| TCT | CTT | GGC | GTT | GAT | ACC | GTG | AAA | CAA | TGG | TCG | GGA | TAT | TTA | GAT | TAC | 653 |
| Ser | Leu | Gly | Val | Asp | Thr | Val | Lys | Gln | Trp | Ser | Gly | Tyr | Leu | Asp | Tyr | |
| | 75 | | | | 80 | | | | | 85 | | | | | | |
| CAG | GAC | TCA | AAA | CAC | TTC | TTT | TAT | TGG | TTT | TTT | GAG | TCT | AGA | AAT | GAC | 701 |
| Gln | Asp | Ser | Lys | His | Phe | Phe | Tyr | Trp | Phe | Phe | Glu | Ser | Arg | Asn | Asp | |
| 90 | | | | | 95 | | | | | 100 | | | | | 105 | |
| CCA | GAG | AAT | GAC | CCA | GTG | ATA | CTA | TGG | TTA | AAC | GGT | GGT | CCT | GGC | TGT | 749 |
| Pro | Glu | Asn | Asp | Pro | Val | Ile | Leu | Trp | Leu | Asn | Gly | Gly | Pro | Gly | Cys | |
| | | | | 110 | | | | | 115 | | | | | 120 | | |
| TCC | TCT | TTC | GTC | GGT | CTT | TTC | TTT | GAA | TTG | GGA | CCT | TCT | TCT | ATA | GGA | 797 |
| Ser | Ser | Phe | Val | Gly | Leu | Phe | Phe | Glu | Leu | Gly | Pro | Ser | Ser | Ile | Gly | |
| | | | 125 | | | | | 130 | | | | | 135 | | | |
| GCT | GAT | TTG | AAA | CCC | ATT | TAT | AAC | CCC | TAC | TCT | TGG | AAT | TCC | AAC | GCT | 845 |
| Ala | Asp | Leu | Lys | Pro | Ile | Tyr | Asn | Pro | Tyr | Ser | Trp | Asn | Ser | Asn | Ala | |
| | | 140 | | | | | 145 | | | | | 150 | | | | |
| TCT | GTG | ATA | TTC | CTA | GAT | CAG | CCT | GTT | GGT | GTT | GGG | TTC | TCA | TAC | GGT | 893 |
| Ser | Val | Ile | Phe | Leu | Asp | Gln | Pro | Val | Gly | Val | Gly | Phe | Ser | Tyr | Gly | |
| | 155 | | | | | 160 | | | | | 165 | | | | | |
| GAC | TCT | AAA | GTG | TCT | ACT | ACA | GAT | GAC | GCT | GCC | AAA | GAC | GTT | TAC | ATA | 941 |
| Asp | Ser | Lys | Val | Ser | Thr | Thr | Asp | Asp | Ala | Ala | Lys | Asp | Val | Tyr | Ile | |
| 170 | | | | | 175 | | | | | 180 | | | | | 185 | |
| TTC | TTA | GAT | TTG | TTC | TTT | GAA | AGA | TTC | CCT | CAT | TTG | AGA | AAT | AAC | GAT | 989 |
| Phe | Leu | Asp | Leu | Phe | Phe | Glu | Arg | Phe | Pro | His | Leu | Arg | Asn | Asn | Asp | |
| | | | | 190 | | | | | 195 | | | | | 200 | | |
| TTC | CAT | ATC | TCC | GGT | GAA | TCA | TAC | GCC | GGT | CAT | TAT | TTA | CCC | AAG | ATT | 1037 |
| Phe | His | Ile | Ser | Gly | Glu | Ser | Tyr | Ala | Gly | His | Tyr | Leu | Pro | Lys | Ile | |
| | | | 205 | | | | | 210 | | | | | 215 | | | |
| GCT | CAT | GAG | ATT | GCT | GTA | GTG | CAT | GCT | GAG | GAT | TCC | TCC | TTC | AAT | CTA | 1085 |
| Ala | His | Glu | Ile | Ala | Val | Val | His | Ala | Glu | Asp | Ser | Ser | Phe | Asn | Leu | |
| | | 220 | | | | | 225 | | | | | 230 | | | | |
| TCG | TCA | GTA | TTA | ATT | GGA | AAT | GGA | TTT | ACT | GAC | CCA | CTG | ACT | CAA | TAC | 1133 |
| Ser | Ser | Val | Leu | Ile | Gly | Asn | Gly | Phe | Thr | Asp | Pro | Leu | Thr | Gln | Tyr | |
| | 235 | | | | | 240 | | | | | 245 | | | | | |
| CAA | TAT | TAC | GAG | CCG | ATG | GCC | TGT | GGT | GAA | GGT | GGT | TAT | CCA | GCG | GTG | 1181 |
| Gln | Tyr | Tyr | Glu | Pro | Met | Ala | Cys | Gly | Glu | Gly | Gly | Tyr | Pro | Ala | Val | |
| 250 | | | | | 255 | | | | | 260 | | | | | 265 | |
| TTG | GAA | CCG | GAA | GAT | TGC | TTA | GAT | ATG | AAT | AGG | AAT | CTA | CCT | CTA | TGC | 1229 |
| Leu | Glu | Pro | Glu | Asp | Cys | Leu | Asp | Met | Asn | Arg | Asn | Leu | Pro | Leu | Cys | |
| | | | | 270 | | | | | 275 | | | | | 280 | | |
| CTA | TCG | CTT | GTG | GAC | CGC | TGT | TAC | AAG | TCC | CAT | TCT | GTT | TTC | TCT | TGT | 1277 |
| Leu | Ser | Leu | Val | Asp | Arg | Cys | Tyr | Lys | Ser | His | Ser | Val | Phe | Ser | Cys | |
| | | | 285 | | | | | 290 | | | | | 295 | | | |
| GTG | TTG | GCT | GAC | CGT | TAT | TGT | GAA | CAA | CAG | ATT | ACT | GGG | GTT | TAT | GAG | 1325 |
| Val | Leu | Ala | Asp | Arg | Tyr | Cys | Glu | Gln | Gln | Ile | Thr | Gly | Val | Tyr | Glu | |
| | | 300 | | | | | 305 | | | | | 310 | | | | |
| AAA | TCA | GGT | AGG | AAC | CCT | TAC | GAT | ATT | AGA | TCT | AAG | TGT | GAA | GCA | GAG | 1373 |
| Lys | Ser | Gly | Arg | Asn | Pro | Tyr | Asp | Ile | Arg | Ser | Lys | Cys | Glu | Ala | Glu | |
| | 315 | | | | | 320 | | | | | 325 | | | | | |
| GAT | GAT | TCC | GGT | GCC | TGT | TAT | CAG | GAA | GAA | ATT | TAT | ATC | TCT | GAT | TAC | 1421 |
| Asp | Asp | Ser | Gly | Ala | Cys | Tyr | Gln | Glu | Glu | Ile | Tyr | Ile | Ser | Asp | Tyr | |

-continued

```
       330                    335                    340                    345
TTG  AAT  CAG  GAG  GAA  GTT  CAA  AGA  GCT  TTA  GGG  ACT  GAT  GTG  AGT  TCT      1469
Leu  Asn  Gln  Glu  Glu  Val  Gln  Arg  Ala  Leu  Gly  Thr  Asp  Val  Ser  Ser
               350                    355                         360

TTC  CAA  GGT  TGT  AGC  TCG  GAT  GTC  GGT  ATC  GGT  TTC  GCA  TTC  ACT  GGC      1517
Phe  Gln  Gly  Cys  Ser  Ser  Asp  Val  Gly  Ile  Gly  Phe  Ala  Phe  Thr  Gly
               365                    370                         375

GAT  GGA  CCG  AGC  CCA  TTC  CAC  CAG  TAC  GTC  GCA  GAA  CTT  CTT  GAT  CAA      1565
Asp  Gly  Pro  Ser  Pro  Phe  His  Gln  Tyr  Val  Ala  Glu  Leu  Leu  Asp  Gln
               380                    385                         390

GAT  ATC  AAT  GTC  TTG  ATA  TAT  GCA  GGC  GAT  AAG  GAT  TAT  ATT  TGT  AAT      1613
Asp  Ile  Asn  Val  Leu  Ile  Tyr  Ala  Gly  Asp  Lys  Asp  Tyr  Ile  Cys  Asn
               395                    400                         405

TGG  CTA  GGA  AAT  CTC  GCT  TGG  ACT  GAA  AAA  TTG  GAA  TGG  AGG  TAT  AAC      1661
Trp  Leu  Gly  Asn  Leu  Ala  Trp  Thr  Glu  Lys  Leu  Glu  Trp  Arg  Tyr  Asn
410                      415                    420                         425

GAA  GAG  TAT  AAA  AAA  CAA  GTT  TTG  AGA  ACT  TGG  AAG  AGT  GAA  GAA  ACA      1709
Glu  Glu  Tyr  Lys  Lys  Gln  Val  Leu  Arg  Thr  Trp  Lys  Ser  Glu  Glu  Thr
               430                    435                         440

GAT  GAG  ACC  ATT  GGC  GAA  ACC  AAA  TCT  TAT  GGC  CCG  CTA  ACT  TAC  TTG      1757
Asp  Glu  Thr  Ile  Gly  Glu  Thr  Lys  Ser  Tyr  Gly  Pro  Leu  Thr  Tyr  Leu
                    445                    450                    455

AGA  ATC  TAT  GAT  GCT  GGA  CAC  ATG  GTT  CCT  CAC  GAC  CAA  CCT  GAA  AAT      1805
Arg  Ile  Tyr  Asp  Ala  Gly  His  Met  Val  Pro  His  Asp  Gln  Pro  Glu  Asn
               460                    465                         470

TCA  TTA  CAA  ATG  GTG  AAT  TCA  TGG  ATT  CAG  AAT  ATC  GCA  AAG  AGA  TCT      1853
Ser  Leu  Gln  Met  Val  Asn  Ser  Trp  Ile  Gln  Asn  Ile  Ala  Lys  Arg  Ser
     475                         480                    485

AGA  ATA  TAAGCATATT TCTTTACAAT TAATTTTAAA TACAAGCACC CTGAGGTATA             1909
Arg  Ile
490

TACTGTATGC  AGTTTGTTGC  ATATCTATCA  TTTCTTTCGC  AATTGTTCAC  TTTTGATTCA       1969

TTCTGTACAC  TCTAATAAGG  TTTTGCAACC  TAGTAATGAT  TCCACACAT   TCTTCAGCCG       2029

ACACAGCTTC  GAAATAATAT  CTCCGTTCTC  TATCAGGTCT  GTGAACAAAA  ATCTTGAAAT       2089

ATTCTGGAAC  GCGCTTAGAC  CTTTTCACCA  GGGTAATTTG  GCTTATATGG  AACGATTTCG       2149

TCTTGACGTT  TTCGTGTGTC  CAATTGAAAT  CACCATCAGG  CCCACTTATA  TAAACGTAGT       2209

CACCATCAAT  GACCAACATC  CTCTCGTGTT  TATTGATGAA  TGACATTTGT  TGTCTTCTCC       2269

ATACCTTATA  TTTATAGTAG  GAACCAGCAA  AGAGATCTTT  GTAACTGTTA  TTTCCAGAAA       2329

CGTTATTTGA  TGGTTTGGAT  AAACTCCCAA  GTTAGGAGA   TTTCTGGCCA  TTGTTGAGAG       2389

AAGATTTTGA  GGAATTTTTG  AGTTAAAAA   AGCCAGAGGT  AGAGGAAGAT  GTGTTATGCT       2449

GCTTGTTGAT  ACTGAATAAA  TTCTTTGAGC  TTGTTCTGTT  CGAGGTTGGT  CGAC             2503
```

( 2 ) INFORMATION FOR SEQ ID NO:4:

( i ) SEQUENCE CHARACTERISTICS:
      ( A ) LENGTH: 491 amino acids
      ( B ) TYPE: amino acid
      ( D ) TOPOLOGY: linear ( i i ) MOLECULE TYPE: protein ( x i ) SEQUENCE DESCRIPTION: SEQ ID NO:4:

```
Met  Val  Ser  Ile  Lys  Phe  Leu  Leu  Ser  Leu  Tyr  Gly  Trp  Leu  Ser  Val
  1                 5                        10                        15

Thr  Leu  Ala  Ile  Ser  Leu  Asn  Ala  Val  Val  Asp  Ser  Leu  Phe  Ser  Asn
                20                       25                        30
```

| Ser | Phe | Asp | Gly | Asn | Asn | Asn | Ile | Glu | Asp | His | Glu | Thr | Ala | Asn | Tyr |
|||||||||||||||||
| | | 35 | | | | | 40 | | | | | 45 | | | |

| Asn | Thr | Gln | Phe | Ser | Val | Phe | Ser | Ser | Asn | Ile | Asp | Asp | Ala | Tyr | Ser |
|||||||||||||||||
| | | 50 | | | | 55 | | | | | 60 | | | | |

| Leu | Arg | Ile | Lys | Pro | Leu | Asp | Pro | Lys | Ser | Leu | Gly | Val | Asp | Thr | Val |
|||||||||||||||||
| 65 | | | | | 70 | | | | | 75 | | | | | 80 |

| Lys | Gln | Trp | Ser | Gly | Tyr | Leu | Asp | Tyr | Gln | Asp | Ser | Lys | His | Phe | Phe |
|||||||||||||||||
| | | | | 85 | | | | | 90 | | | | | 95 | |

| Tyr | Trp | Phe | Phe | Glu | Ser | Arg | Asn | Asp | Pro | Glu | Asn | Asp | Pro | Val | Ile |
|||||||||||||||||
| | | | 100 | | | | | 105 | | | | | 110 | | |

| Leu | Trp | Leu | Asn | Gly | Gly | Pro | Gly | Cys | Ser | Ser | Phe | Val | Gly | Leu | Phe |
|||||||||||||||||
| | | | 115 | | | | | 120 | | | | | 125 | | |

| Phe | Glu | Leu | Gly | Pro | Ser | Ser | Ile | Gly | Ala | Asp | Leu | Lys | Pro | Ile | Tyr |
|||||||||||||||||
| | 130 | | | | | 135 | | | | | 140 | | | | |

| Asn | Pro | Tyr | Ser | Trp | Asn | Ser | Asn | Ala | Ser | Val | Ile | Phe | Leu | Asp | Gln |
|||||||||||||||||
| 145 | | | | | 150 | | | | | 155 | | | | | 160 |

| Pro | Val | Gly | Val | Gly | Phe | Ser | Tyr | Gly | Asp | Ser | Lys | Val | Ser | Thr | Thr |
|||||||||||||||||
| | | | | 165 | | | | | 170 | | | | | 175 | |

| Asp | Asp | Ala | Ala | Lys | Asp | Val | Tyr | Ile | Phe | Leu | Asp | Leu | Phe | Phe | Glu |
|||||||||||||||||
| | | | 180 | | | | | 185 | | | | | 190 | | |

| Arg | Phe | Pro | His | Leu | Arg | Asn | Asn | Asp | Phe | His | Ile | Ser | Gly | Glu | Ser |
|||||||||||||||||
| | | 195 | | | | | 200 | | | | | 205 | | | |

| Tyr | Ala | Gly | His | Tyr | Leu | Pro | Lys | Ile | Ala | His | Glu | Ile | Ala | Val | Val |
|||||||||||||||||
| | 210 | | | | | 215 | | | | | 220 | | | | |

| His | Ala | Glu | Asp | Ser | Ser | Phe | Asn | Leu | Ser | Ser | Val | Leu | Ile | Gly | Asn |
|||||||||||||||||
| 225 | | | | | 230 | | | | | 235 | | | | | 240 |

| Gly | Phe | Thr | Asp | Pro | Leu | Thr | Gln | Tyr | Gln | Tyr | Tyr | Glu | Pro | Met | Ala |
|||||||||||||||||
| | | | | 245 | | | | | 250 | | | | | 255 | |

| Cys | Gly | Glu | Gly | Gly | Tyr | Pro | Ala | Val | Leu | Glu | Pro | Glu | Asp | Cys | Leu |
|||||||||||||||||
| | | | 260 | | | | | 265 | | | | | 270 | | |

| Asp | Met | Asn | Arg | Asn | Leu | Pro | Leu | Cys | Leu | Ser | Leu | Val | Asp | Arg | Cys |
|||||||||||||||||
| | | 275 | | | | | 280 | | | | | 285 | | | |

| Tyr | Lys | Ser | His | Ser | Val | Phe | Ser | Cys | Val | Leu | Ala | Asp | Arg | Tyr | Cys |
|||||||||||||||||
| | 290 | | | | | 295 | | | | | 300 | | | | |

| Glu | Gln | Gln | Ile | Thr | Gly | Val | Tyr | Glu | Lys | Ser | Gly | Arg | Asn | Pro | Tyr |
|||||||||||||||||
| 305 | | | | | 310 | | | | | 315 | | | | | 320 |

| Asp | Ile | Arg | Ser | Lys | Cys | Glu | Ala | Glu | Asp | Asp | Ser | Gly | Ala | Cys | Tyr |
|||||||||||||||||
| | | | | 325 | | | | | 330 | | | | | 335 | |

| Gln | Glu | Glu | Ile | Tyr | Ile | Ser | Asp | Tyr | Leu | Asn | Gln | Glu | Glu | Val | Gln |
|||||||||||||||||
| | | | 340 | | | | | 345 | | | | | 350 | | |

| Arg | Ala | Leu | Gly | Thr | Asp | Val | Ser | Ser | Phe | Gln | Gly | Cys | Ser | Ser | Asp |
|||||||||||||||||
| | | 355 | | | | | 360 | | | | | 365 | | | |

| Val | Gly | Ile | Gly | Phe | Ala | Phe | Thr | Gly | Asp | Gly | Pro | Ser | Pro | Phe | His |
|||||||||||||||||
| | 370 | | | | | 375 | | | | | 380 | | | | |

| Gln | Tyr | Val | Ala | Glu | Leu | Leu | Asp | Gln | Asp | Ile | Asn | Val | Leu | Ile | Tyr |
|||||||||||||||||
| 385 | | | | | 390 | | | | | 395 | | | | | 400 |

| Ala | Gly | Asp | Lys | Asp | Tyr | Ile | Cys | Asn | Trp | Leu | Gly | Asn | Leu | Ala | Trp |
|||||||||||||||||
| | | | | 405 | | | | | 410 | | | | | 415 | |

| Thr | Glu | Lys | Leu | Glu | Trp | Arg | Tyr | Asn | Glu | Glu | Tyr | Lys | Lys | Gln | Val |
|||||||||||||||||
| | | | 420 | | | | | 425 | | | | | 430 | | |

| Leu | Arg | Thr | Trp | Lys | Ser | Glu | Glu | Thr | Asp | Glu | Thr | Ile | Gly | Glu | Thr |
|||||||||||||||||
| | | 435 | | | | | 440 | | | | | 445 | | | |

| Lys | Ser | Tyr | Gly | Pro | Leu | Thr | Tyr | Leu | Arg | Ile | Tyr | Asp | Ala | Gly | His |
|||||||||||||||||
| | 450 | | | | | 455 | | | | | 460 | | | | |

```
Met Val Pro His Asp Gln Pro Glu Asn Ser Leu Gln Met Val Asn Ser
465                 470                 475                 480

Trp Ile Gln Asn Ile Ala Lys Arg Ser Arg Ile
            485                 490
```

( 2 ) INFORMATION FOR SEQ ID NO:5:

( i ) SEQUENCE CHARACTERISTICS:
        ( A ) LENGTH: 1615 base pairs
        ( B ) TYPE: nucleic acid
        ( C ) STRANDEDNESS: double
        ( D ) TOPOLOGY: linear ( i i ) MOLECULE TYPE: cDNA ( v i ) ORIGINAL SOURCE:
        ( A ) ORGANISM: Kluyveromyces lactis ( i x ) FEATURE:
        ( A ) NAME/KEY: CDS
        ( B ) LOCATION: 188..1417
        ( D ) OTHER INFORMATION: /product="Protease A Gene"
        / gene="PRA1"

( x i ) SEQUENCE DESCRIPTION: SEQ ID NO:5:

```
ATCGATAATA GAAGTGTTGA CATAACTATA TTAAAGACAG GGTAGACGGT CAGATATATA      60

GTAGTGTCAG TATTTTGAAC GGAGAGGAAC TTGATTAAAT CTATTATACA GTTTCCCCCA     120

AAATTTTTCT GAAATTGTGC CGCTAACTGT TCATTAAACG GTGCTTCTT ACAACAAAAA     180

AATAAGC ATG CAT TTG AAT TTC CAA TCT CTT TTG CCT CTA GCT TCA TTG       229
        Met His Leu Asn Phe Gln Ser Leu Leu Pro Leu Ala Ser Leu
          1               5                  10

TTA TTG GCT TCT TTT GAT GTT GCT GAA GCC AAG ATT CAT AAG GCC AAA       277
Leu Leu Ala Ser Phe Asp Val Ala Glu Ala Lys Ile His Lys Ala Lys
 15              20                  25                  30

ATT CAA AAA CAT AAA TTG GAA GAC CAA TTG AAG GAT GTT CCA TTT GCC       325
Ile Gln Lys His Lys Leu Glu Asp Gln Leu Lys Asp Val Pro Phe Ala
                 35                  40                  45

GAA CAT GTG GCT CAA CTA GGT GAA AAG TAC TTA AAT AGC TTC CAA AGA       373
Glu His Val Ala Gln Leu Gly Glu Lys Tyr Leu Asn Ser Phe Gln Arg
             50                  55                  60

GCT TAC CCT CAA GAA TCT TTC TCT AAG GAT AAC GTT GAT GTT TTC GTT       421
Ala Tyr Pro Gln Glu Ser Phe Ser Lys Asp Asn Val Asp Val Phe Val
         65                  70                  75

GCC CCA GAA GGG TCT CAC AGT GTC CCA TTG ACC AAT TAC TTG AAT GCT       469
Ala Pro Glu Gly Ser His Ser Val Pro Leu Thr Asn Tyr Leu Asn Ala
     80                  85                  90

CAG TAT TTC ACA GAA ATT ACT TTG GGT TCG CCA CCA CAG TCT TTT AAG       517
Gln Tyr Phe Thr Glu Ile Thr Leu Gly Ser Pro Pro Gln Ser Phe Lys
 95                 100                 105                 110

GTT ATC TTA GAC ACT GGT TCA TCA AAC TTG TGG GTT CCA AGT GCA GAA       565
Val Ile Leu Asp Thr Gly Ser Ser Asn Leu Trp Val Pro Ser Ala Glu
                115                 120                 125

TGT GGT TCT TTG GCA TGT TTC TTG CAC ACC AAA TAT GAC CAT GAG GCT       613
Cys Gly Ser Leu Ala Cys Phe Leu His Thr Lys Tyr Asp His Glu Ala
            130                 135                 140

TCT AGC ACT TAC AAA GCT AAT GGT TCC GAG TTT GCT ATC CAA TAT GGT       661
Ser Ser Thr Tyr Lys Ala Asn Gly Ser Glu Phe Ala Ile Gln Tyr Gly
        145                 150                 155

TCT GGT TCC CTT GAA GGA TAT GTG TCT CGT GAT TTG TTG ACC ATT GGG       709
Ser Gly Ser Leu Glu Gly Tyr Val Ser Arg Asp Leu Leu Thr Ile Gly
    160                 165                 170

GAT TTA GTG ATA CCT GAC CAG GAT TTC GCT GAA GCT ACC AGC GAA CCA       757
```

-continued

| | | | | | | | | | | | | | | | | |
|---|---|---|---|---|---|---|---|---|---|---|---|---|---|---|---|---|
| Asp | Leu | Val | Ile | Pro | Asp | Gln | Asp | Phe | Ala | Glu | Ala | Thr | Ser | Glu | Pro | |
| 175 | | | | 180 | | | | | 185 | | | | | 190 | | |

| GGT | TTG | GCA | TTT | GCC | TTT | GGT | AAA | TTC | GAT | GGT | ATT | TTG | GGG | TTG | GCT | 805 |
|---|---|---|---|---|---|---|---|---|---|---|---|---|---|---|---|---|
| Gly | Leu | Ala | Phe | Ala | Phe | Gly | Lys | Phe | Asp | Gly | Ile | Leu | Gly | Leu | Ala | |
| | | | | 195 | | | | | 200 | | | | | 205 | | |

| TAC | GAC | TCC | ATC | TCT | GTT | AAC | AGA | ATC | GTT | CCA | CCA | GTG | TAC | AAC | GCT | 853 |
|---|---|---|---|---|---|---|---|---|---|---|---|---|---|---|---|---|
| Tyr | Asp | Ser | Ile | Ser | Val | Asn | Arg | Ile | Val | Pro | Pro | Val | Tyr | Asn | Ala | |
| | | | 210 | | | | | 215 | | | | | 220 | | | |

| ATC | AAA | AAC | AAA | CTT | TTG | GAT | GAC | CCA | GTG | TTT | GCC | TTT | TAC | TTG | GGT | 901 |
|---|---|---|---|---|---|---|---|---|---|---|---|---|---|---|---|---|
| Ile | Lys | Asn | Lys | Leu | Leu | Asp | Asp | Pro | Val | Phe | Ala | Phe | Tyr | Leu | Gly | |
| | | 225 | | | | | 230 | | | | | 235 | | | | |

| GAT | TCT | GAC | AAG | TCT | GAA | GAT | GGC | GGT | GAA | GCT | TCC | TTC | GGT | GGT | ATC | 949 |
|---|---|---|---|---|---|---|---|---|---|---|---|---|---|---|---|---|
| Asp | Ser | Asp | Lys | Ser | Glu | Asp | Gly | Gly | Glu | Ala | Ser | Phe | Gly | Gly | Ile | |
| 240 | | | | | 245 | | | | | 250 | | | | | | |

| GAT | GAG | GAG | AAG | TAC | ACC | GGT | GAA | ATC | ACT | TGG | TTG | CCT | GTT | CGT | CGT | 997 |
|---|---|---|---|---|---|---|---|---|---|---|---|---|---|---|---|---|
| Asp | Glu | Glu | Lys | Tyr | Thr | Gly | Glu | Ile | Thr | Trp | Leu | Pro | Val | Arg | Arg | |
| 255 | | | | 260 | | | | | 265 | | | | | 270 | | |

| AAG | GCT | TAC | TGG | GAA | GTC | AAG | TTT | GAA | GGT | ATC | GGT | TTG | GGT | GAA | GAA | 1045 |
|---|---|---|---|---|---|---|---|---|---|---|---|---|---|---|---|---|
| Lys | Ala | Tyr | Trp | Glu | Val | Lys | Phe | Glu | Gly | Ile | Gly | Leu | Gly | Glu | Glu | |
| | | | | 275 | | | | | 280 | | | | | 285 | | |

| TAT | GCT | ACT | TTA | GAA | GGT | CAT | GGT | GCT | GCT | ATC | GAC | ACC | GGT | ACC | TCT | 1093 |
|---|---|---|---|---|---|---|---|---|---|---|---|---|---|---|---|---|
| Tyr | Ala | Thr | Leu | Glu | Gly | His | Gly | Ala | Ala | Ile | Asp | Thr | Gly | Thr | Ser | |
| | | | 290 | | | | | 295 | | | | | 300 | | | |

| TTG | ATT | GCT | TTG | CCA | AGC | GGT | TTG | GCT | GAA | ATT | TTG | AAC | GCT | GAA | ATC | 1141 |
|---|---|---|---|---|---|---|---|---|---|---|---|---|---|---|---|---|
| Leu | Ile | Ala | Leu | Pro | Ser | Gly | Leu | Ala | Glu | Ile | Leu | Asn | Ala | Glu | Ile | |
| | | 305 | | | | | 310 | | | | | 315 | | | | |

| GGT | GCA | AAG | AAG | GGC | TGG | TCT | GGT | CAA | TAC | TCC | GTT | GAT | TGT | GAA | TCT | 1189 |
|---|---|---|---|---|---|---|---|---|---|---|---|---|---|---|---|---|
| Gly | Ala | Lys | Lys | Gly | Trp | Ser | Gly | Gln | Tyr | Ser | Val | Asp | Cys | Glu | Ser | |
| 320 | | | | | 325 | | | | | 330 | | | | | | |

| AGA | GAT | AGT | CTA | CCA | GAC | TTA | ACT | TTG | AAT | TTC | AAC | GGT | TAC | AAC | TTC | 1237 |
|---|---|---|---|---|---|---|---|---|---|---|---|---|---|---|---|---|
| Arg | Asp | Ser | Leu | Pro | Asp | Leu | Thr | Leu | Asn | Phe | Asn | Gly | Tyr | Asn | Phe | |
| 335 | | | | | 340 | | | | | 345 | | | | | 350 | |

| ACT | ATT | ACC | GCA | TAC | GAT | TAC | ACT | TTG | GAA | GTC | TCT | GGG | TCT | TGT | ATC | 1285 |
|---|---|---|---|---|---|---|---|---|---|---|---|---|---|---|---|---|
| Thr | Ile | Thr | Ala | Tyr | Asp | Tyr | Thr | Leu | Glu | Val | Ser | Gly | Ser | Cys | Ile | |
| | | | | 355 | | | | | 360 | | | | | 365 | | |

| TCT | GCA | TTC | ACT | CCA | ATG | GAC | TTC | CCA | GAA | CCA | GTT | GGT | CCC | TTG | GCC | 1333 |
|---|---|---|---|---|---|---|---|---|---|---|---|---|---|---|---|---|
| Ser | Ala | Phe | Thr | Pro | Met | Asp | Phe | Pro | Glu | Pro | Val | Gly | Pro | Leu | Ala | |
| | | | 370 | | | | | 375 | | | | | 380 | | | |

| ATT | ATT | GGT | GAT | GCC | TTC | CTA | CGT | AAA | TAC | TAC | TCC | ATT | TAT | GAT | ATT | 1381 |
|---|---|---|---|---|---|---|---|---|---|---|---|---|---|---|---|---|
| Ile | Ile | Gly | Asp | Ala | Phe | Leu | Arg | Lys | Tyr | Tyr | Ser | Ile | Tyr | Asp | Ile | |
| | | 385 | | | | | 390 | | | | | 395 | | | | |

| GGT | CAT | GAT | GCA | GTT | GGT | TTG | GCC | AAG | GCT | GCC | | TAATTGTTAA | AAAAGCGATC | | | 1434 |
|---|---|---|---|---|---|---|---|---|---|---|---|---|---|---|---|---|
| Gly | His | Asp | Ala | Val | Gly | Leu | Ala | Lys | Ala | Ala | | | | | | |
| | 400 | | | | 405 | | | | | 410 | | | | | | |

| GAATTGTAAC | CTTTTGAATT | GGAGTTCAGC | TTCTATTAAC | TCGACAACTC | TAAAAAAATA | 1494 |
|---|---|---|---|---|---|---|
| ATTAAATAAG | ACGGTTAACT | TACTGCTATA | TTAATTGAAT | GTCAGTTTCA | CAAATCGAAT | 1554 |
| TAGCTAACAA | AGTATAACAA | CACTTGGTGA | CAAATAAACC | TTAAAATACC | TGGCAGAATT | 1614 |
| C | | | | | | 1615 |

( 2 ) INFORMATION FOR SEQ ID NO:6:

( i ) SEQUENCE CHARACTERISTICS:
        ( A ) LENGTH: 409 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

Met  His  Leu  Asn  Phe  Gln  Ser  Leu  Leu  Pro  Leu  Ala  Ser  Leu  Leu  Leu

```
  1                    5                         10                        15
Ala  Ser  Phe  Asp  Val  Ala  Glu  Ala  Lys  Ile  His  Lys  Ala  Lys  Ile  Gln
               20                      25                     30
Lys  His  Lys  Leu  Glu  Asp  Gln  Leu  Lys  Asp  Val  Pro  Phe  Ala  Glu  His
          35                      40                      45
Val  Ala  Gln  Leu  Gly  Glu  Lys  Tyr  Leu  Asn  Ser  Phe  Gln  Arg  Ala  Tyr
     50                      55                      60
Pro  Gln  Glu  Ser  Phe  Ser  Lys  Asp  Asn  Val  Asp  Val  Phe  Val  Ala  Pro
65                       70                      75                           80
Glu  Gly  Ser  His  Ser  Val  Pro  Leu  Thr  Asn  Tyr  Leu  Asn  Ala  Gln  Tyr
                    85                      90                      95
Phe  Thr  Glu  Ile  Thr  Leu  Gly  Ser  Pro  Pro  Gln  Ser  Phe  Lys  Val  Ile
               100                     105                     110
Leu  Asp  Thr  Gly  Ser  Ser  Asn  Leu  Trp  Val  Pro  Ser  Ala  Glu  Cys  Gly
          115                     120                     125
Ser  Leu  Ala  Cys  Phe  Leu  His  Thr  Lys  Tyr  Asp  His  Glu  Ala  Ser  Ser
     130                     135                     140
Thr  Tyr  Lys  Ala  Asn  Gly  Ser  Glu  Phe  Ala  Ile  Gln  Tyr  Gly  Ser  Gly
145                      150                     155                          160
Ser  Leu  Glu  Gly  Tyr  Val  Ser  Arg  Asp  Leu  Leu  Thr  Ile  Gly  Asp  Leu
                    165                     170                     175
Val  Ile  Pro  Asp  Gln  Asp  Phe  Ala  Glu  Ala  Thr  Ser  Glu  Pro  Gly  Leu
               180                     185                     190
Ala  Phe  Ala  Phe  Gly  Lys  Phe  Asp  Gly  Ile  Leu  Gly  Leu  Ala  Tyr  Asp
          195                     200                     205
Ser  Ile  Ser  Val  Asn  Arg  Ile  Val  Pro  Pro  Val  Tyr  Asn  Ala  Ile  Lys
     210                     215                     220
Asn  Lys  Leu  Leu  Asp  Asp  Pro  Val  Phe  Ala  Phe  Tyr  Leu  Gly  Asp  Ser
225                      230                     235                          240
Asp  Lys  Ser  Glu  Asp  Gly  Gly  Glu  Ala  Ser  Phe  Gly  Gly  Ile  Asp  Glu
                    245                     250                     255
Glu  Lys  Tyr  Thr  Gly  Glu  Ile  Thr  Trp  Leu  Pro  Val  Arg  Arg  Lys  Ala
               260                     265                     270
Tyr  Trp  Glu  Val  Lys  Phe  Glu  Gly  Ile  Gly  Leu  Gly  Glu  Glu  Tyr  Ala
          275                     280                     285
Thr  Leu  Glu  Gly  His  Gly  Ala  Ala  Ile  Asp  Thr  Gly  Thr  Ser  Leu  Ile
     290                     295                     300
Ala  Leu  Pro  Ser  Gly  Leu  Ala  Glu  Ile  Leu  Asn  Ala  Glu  Ile  Gly  Ala
305                      310                     315                          320
Lys  Lys  Gly  Trp  Ser  Gly  Gln  Tyr  Ser  Val  Asp  Cys  Glu  Ser  Arg  Asp
                    325                     330                     335
Ser  Leu  Pro  Asp  Leu  Thr  Leu  Asn  Phe  Asn  Gly  Tyr  Asn  Phe  Thr  Ile
               340                     345                     350
Thr  Ala  Tyr  Asp  Tyr  Thr  Leu  Glu  Val  Ser  Gly  Ser  Cys  Ile  Ser  Ala
          355                     360                     365
Phe  Thr  Pro  Met  Asp  Phe  Pro  Glu  Pro  Val  Gly  Pro  Leu  Ala  Ile  Ile
     370                     375                     380
Gly  Asp  Ala  Phe  Leu  Arg  Lys  Tyr  Tyr  Ser  Ile  Tyr  Asp  Ile  Gly  His
385                      390                     395                          400
Asp  Ala  Val  Gly  Leu  Ala  Lys  Ala  Ala
                    405
```

( 2 ) INFORMATION FOR SEQ ID NO:7:

(i) SEQUENCE CHARACTERISTICS:
  (A) LENGTH: 224 amino acids
  (B) TYPE: amino acid
  (D) TOPOLOGY: linear (ii) MOLECULE TYPE: peptide (v) FRAGMENT TYPE: internal (vi) ORIGINAL SOURCE:
  (A) ORGANISM: Kluyveromyces lactis (xi) SEQUENCE DESCRIPTION: SEQ ID NO:7:

```
Arg Ser Asn Gly Ser Gly Thr Met Ser Asp Val Val Lys Gly Val Glu
 1               5                  10                  15

Tyr Val Ala Glu Ala His Lys Lys Ala Val Glu Glu Gln Lys Lys Gly
            20                  25                  30

Phe Lys Gly Ser Thr Ala Asn Met Ser Leu Gly Gly Gly Lys Ser Pro
        35                  40                  45

Ala Leu Asp Leu Ala Val Asn Ala Ala Val Lys Ala Gly Val His Phe
    50                  55                  60

Ala Val Ala Ala Gly Asn Glu Asn Gln Asp Ala Cys Asn Thr Ser Pro
65                  70                  75                  80

Ala Ala Ala Glu Asn Ala Ile Thr Val Gly Ala Ser Thr Leu Ser Asp
                85                  90                  95

Glu Arg Ala Tyr Phe Ser Asn Trp Gly Lys Cys Val Asp Ile Phe Gly
            100                 105                 110

Pro Gly Leu Asn Ile Leu Ser Thr Tyr Ile Gly Ser Asp Thr Ala Thr
        115                 120                 125

Ala Thr Leu Ser Gly Thr Ser Met Ala Thr Pro His Val Val Gly Leu
    130                 135                 140

Leu Thr Tyr Phe Leu Ser Leu Gln Pro Asp Ala Asp Ser Glu Tyr Phe
145                 150                 155                 160

His Ala Ala Gly Gly Ile Thr Pro Ser Gln Leu Lys Lys Lys Leu Ile
                165                 170                 175

Asp Phe Ser Thr Lys Asn Val Leu Ser Asp Leu Pro Glu Asp Thr Val
            180                 185                 190

Asn Tyr Leu Ile Tyr Asn Gly Gly Gly Gln Asp Leu Asp Asp Leu Trp
        195                 200                 205

Gly Lys Asp Tyr Ser Ile Gly Lys Glu Pro Ser Ala Asn Pro Glu Phe
    210                 215                 220
```

(2) INFORMATION FOR SEQ ID NO:8:

(i) SEQUENCE CHARACTERISTICS:
    (A) LENGTH: 225 amino acids
    (B) TYPE: amino acid
    (D) TOPOLOGY: linear (ii) MOLECULE TYPE: peptide (v) FRAGMENT TYPE: internal (vi) ORIGINAL SOURCE:
    (A) ORGANISM: Saccharomyces cerevisiae (xi) SEQUENCE DESCRIPTION: SEQ ID NO:8:

```
Arg Ser Asn Gly Ser Gly Thr Met Ser Asp Val Val Lys Gly Val Glu
 1               5                  10                  15

Tyr Ala Ala Lys Ala His Gln Lys Glu Ala Gln Glu Lys Lys Lys Gly
            20                  25                  30

Phe Lys Gly Ser Thr Ala Asn Met Ser Leu Gly Gly Gly Lys Ser Pro
```

|   |   |   |   |   | 35 |   |   |   | 40 |   |   |   |   | 45 |   |   |   |
|---|---|---|---|---|---|---|---|---|---|---|---|---|---|---|---|---|---|
| Ala | Leu 50 | Asp | Leu | Ala | Val | Asn 55 | Ala | Ala | Val | Glu | Val 60 | Gly | Ile | His | Phe |
| Ala 65 | Val | Ala | Ala | Gly | Asn 70 | Glu | Asn | Gln | Asp | Ala 75 | Cys | Asn | Thr | Ser | Pro 80 |
| Ala | Ser | Ala | Glu | Lys 85 | Ala | Ile | Thr | Val | Gly 90 | Ala | Ser | Thr | Leu | Ser 95 | Asp |
| Asp | Arg | Ala | Tyr 100 | Phe | Ser | Asn | Trp | Gly 105 | Lys | Cys | Val | Asp | Val 110 | Phe | Ala |
| Pro | Gly | Leu 115 | Asn | Ile | Leu | Ser | Thr 120 | Tyr | Ile | Gly | Ser | Asp 125 | Ala | Thr |  |
| Ala | Thr 130 | Leu | Ser | Gly | Thr | Ser 135 | Met | Ala | Ser | Pro | His 140 | Val | Ala | Gly | Leu |
| Leu 145 | Thr | Tyr | Phe | Leu | Ser 150 | Leu | Gln | Pro | Gly | Ser 155 | Asp | Ser | Glu | Phe | Phe 160 |
| Glu | Leu | Gly | Glu | Asp 165 | Ser | Leu | Thr | Pro | Gln 170 | Gln | Leu | Lys | Lys | Lys 175 | Leu |
| Ile | His | Tyr | Ser 180 | Thr | Lys | Asp | Ile | Leu 185 | Phe | Asp | Ile | Pro | Glu 190 | Asp | Thr |
| Pro | Asn | Val 195 | Leu | Ile | Tyr | Asn | Gly 200 | Gly | Gly | Gln | Asp | Leu 205 | Ser | Ala | Phe |
| Trp | Asn 210 | Lys | Asp | Thr | Lys | Lys 215 | Ser | His | Ser | Ser | Gly 220 | Phe | Lys | Gln | Glu |
| Leu 225 |   |   |   |   |   |   |   |   |   |   |   |   |   |   |   |

( 2 ) INFORMATION FOR SEQ ID NO:9:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:9:

TGACACTCAA AATAGCG                                                            17

( 2 ) INFORMATION FOR SEQ ID NO:10:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:10:

AATATCTCTC ACTTGAT                                                            17

( 2 ) INFORMATION FOR SEQ ID NO:11:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:11:

GACCTATGGG GTAAGGATTA C                                                                         21

( 2 ) INFORMATION FOR SEQ ID NO:12:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:12:

GCTTCGGCAA CATATTCG                                                                             18

( 2 ) INFORMATION FOR SEQ ID NO:13:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:13:

CTTCTTGGAG TTGTTCTTCG                                                                           20

( 2 ) INFORMATION FOR SEQ ID NO:14:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:14:

TGGCAAGACA TCCGTCCACG CCTTATTACC                                                                 30

( 2 ) INFORMATION FOR SEQ ID NO:15:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:15:

CTGTTGATAA GGTGGTCC                                                                             18

( 2 ) INFORMATION FOR SEQ ID NO:16:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:16:

CAAGCGTGTA ATCGTATGGC                                                                           20

( 2 ) INFORMATION FOR SEQ ID NO:17:

(i) SEQUENCE CHARACTERISTICS:
    (A) LENGTH: 30 base pairs
    (B) TYPE: nucleic acid
    (C) STRANDEDNESS: single
    (D) TOPOLOGY: linear (ii) MOLECULE TYPE: other nucleic acid (xi) SEQUENCE DESCRIPTION: SEQ ID NO:17:

GAAATGCATA AGCTCTTGCC ATTCTCACCG     30